United States Patent
Reiffenrath et al.

Patent Number: 6,017,469
Date of Patent: *Jan. 25, 2000

[54] SUPERTWIST LIQUID-CRYSTAL DISPLAY

[75] Inventors: Volker Reiffenrath, Rossdorf; Bernhard Rieger, Münster; Michael Junge, Pfungstadt; Martina Schmidt, Münster; Christine Pfister, Grossenwiehe, all of Germany

[73] Assignee: Merck Patent Gesellschaft mit Beschrankter Haftung, Germany

[*] Notice: This patent is subject to a terminal disclaimer.

[21] Appl. No.: 08/737,288

[22] PCT Filed: May 8, 1995

[86] PCT No.: PCT/EP95/01740

§ 371 Date: Dec. 1, 1997

§ 102(e) Date: Dec. 1, 1997

[87] PCT Pub. No.: WO95/30723

PCT Pub. Date: Nov. 16, 1995

[30] Foreign Application Priority Data

| May 10, 1994 | [DE] | Germany | 44 16 454 |
| May 10, 1994 | [DE] | Germany | 44 16 455 |
| Sep. 29, 1994 | [DE] | Germany | 44 34 851 |
| Nov. 25, 1994 | [DE] | Germany | 44 41 963 |
| Dec. 1, 1994 | [DE] | Germany | 44 42 842 |
| Mar. 30, 1995 | [DE] | Germany | 195 11 632 |

[51] Int. Cl.[7] .......................... C09K 19/30; C07C 13/19; C07C 19/08; C07C 15/40
[52] U.S. Cl. ................ 252/299.63; 252/299.01; 568/667; 570/128; 585/435
[58] Field of Search ................ 252/299.01, 299.63, 252/299.61; 585/435, 350; 570/128; 568/667

[56] References Cited

U.S. PATENT DOCUMENTS 5,679,285  10/1997  Bartmann et al. ................ 252/299.63

FOREIGN PATENT DOCUMENTS

| 261614 | 3/1988 | European Pat. Off. . |
| 470590 | 2/1992 | European Pat. Off. . |
| 571916 | 12/1993 | European Pat. Off. . |
| 3509170 | 9/1986 | Germany . |
| 9012073 | 10/1990 | WIPO . |
| 9100898 | 1/1991 | WIPO . |

*Primary Examiner*—Shean C. Wu
*Attorney, Agent, or Firm*—Millen, White, Zelane, & Branigan, P.C.

[57] ABSTRACT

Supertwist liquid crystal displays with outstanding properties are obtained when the nematic liquid crystal mixture contains at least one compound of the formula (I):

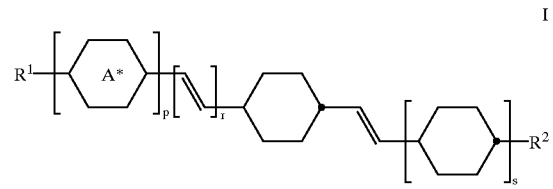

where the variables are as defined in the disclosure.

19 Claims, No Drawings

SUPERTWIST LIQUID-CRYSTAL DISPLAY

This application is a 371 of PCT/EP/01740, filed May 8, 1995.

The invention relates to supertwist liquid-crystal displays (SLCD) having very short response times and good steepnesses and angle dependencies, and to the novel nematic liquid-crystal mixtures used therein.

SLCDs as defined in the preamble are known, for example from EP 0 131 216 B1; DE 34 23 993 A1; EP 0 098 070 A2; M. Schadt and F. Leenhouts, 17th Freiburg Congress on Liquid Crystals (8.–10.04.87); K. Kawasaki et al., SID 87 Digest 391 (20.6); M. Schadt and F. Leenhouts, SID 87 Digest 372 (20.1); K. Katoh et al., Japanese Journal of Applied Physics, Vol. 26, No. 11, L 1784-L 1786 (1987); F. Leenhouts et al., Appl. Phys. Lett. 50 (21), 1468 (1987); H. A. van Sprang and H. G. Koopman, J. Appl. Phys. 62 (5), 1734 (1987); T. J. Scheffer and J. Nehring, Appl. Phys. Lett. 45 (10), 1021 (1984), M. Schadt and F. Leenhouts, Appl. Phys. Lett. 50. (5), 236 (1987) and E. P. Raynes, Mol. Cryst. Liq. Cryst. Letters Vol. 4 (1), pp. 1–8 (1986). The term SLCD here covers any more highly twisted display element with a value for the twist angle of between 160° and 360°, such as, for example, the display elements of Waters et al. (C. M. Waters et al., Proc. Soc. Inf. Disp. (New York) (1985) (3rd Intern. Display Conference, Kobe, Japan), STN-LCDs (DE-A 35 03 259), SBE-LCDs (T. J. Scheffer and J. Nehring, Appl. Phys. Lett. 45 (1984) 1021), OMI-LCDs (M. Schadt and F. Leenhouts, Appl. Phys. Lett. 50 (1987), 236, DST-LCDs (EP-A 0 246 842) or BW-STN-LCDs (K. Kawasaki et al., SID 87 Digest 391 (20.6)).

SLCDs of this type are distinguished, in comparison to standard TN displays, by significantly better steepnesses of the electrooptical characteristic line and consequently better contrast values, and by significantly less angle dependence of the contrast. Of particular interest are SLCDs having very short response times, in particular also at relatively low temperatures. In order to achieve short response times, the viscosities, in particular, of the liquid-crystal mixtures were hitherto optimised using usually monotropic additives having relatively high vapour pressure. However, the response times achieved were not adequate for all applications.

In order to achieve a steep electrooptical characteristic line, the liquid-crystal mixtures should have relatively large values for $K_3/K_1$ and relatively small values for $\Delta\epsilon/\epsilon_1$.

In addition to optimisation of the contrast and the response times, further important requirements are made of mixtures of this type:

1. A broad d/p window
2. High long-term chemical stability,
3. High electrical resistance
4. Low frequency dependence of the threshold voltage.

The parameter combinations achieved are still by far inadequate, in particular for high-multiplex STNs (1/400). This is in some cases attributable to the fact that the various requirements are affected in opposite manners by material parameters.

There thus continues to be a great demand for SLCDs having very short response times and at the same time a large operating temperature range, high characteristic line steepness, good angle dependence of the contrast and low threshold voltage which meet the above-mentioned requirements.

DE 35 09 170 discloses compounds of the formula

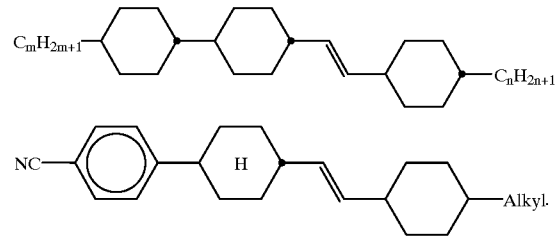

Chemiker Zeitung 104 (1980), 269–271, describes compounds of the formula I containing long-chain alkyl radicals (m+n>9). However, the latter representatives have exclusively smectic phases which are disadvantageous for use in nematic liquid-crystal mixtures. Surprisingly, a nematic phase range and at the same time suppression of the smectic phase were obtained by shortening the chain lengths.

The invention has the object of providing SLCDs which do not have the abovementioned disadvantages, or only do so to a lesser extent, and at the same time have very good steepnesses.

It has now been found that this object can be achieved if nematic liquid-crystal mixtures are used which comprise 1,2-dicyclohexylethylene derivatives of the formula I

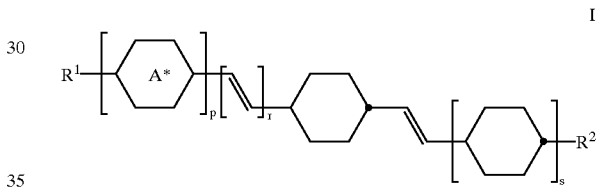

in which

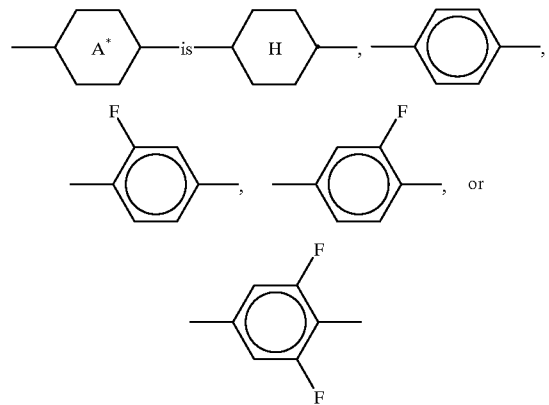

$R^1$ is an alkyl, alkoxy or alkenyl radical having 1 to 10 carbon atoms which is unsubstituted or monosubstituted by CN or $CF_2$ or at least monosubstituted by halogen, it also being possible for one or more $CH_2$ groups in this radical to be replaced by —O—, $R^2$ is $(CH_2)_n$—CH=CH—$R^a$ or $(CH_2)_n$—CH=$CH_2$, and in the case where r=1, $R^2$ alternatively is $R^a$ $R^a$ is a straight-chain alkyl having 1–6 carbon atoms, n is 0–6, p and r are each, independently of one another, 0 or 1, and s is 1 or 2.

The compounds of the formula I significantly increase the steepness characteristics of STN mixtures without increasing the response times.

The invention thus relates to an SLCD containing two plane-parallel outer plates which, together with a frame, form a cell, a nematic liquid-crystal mixture of positive dielectric anisotropy which is present in the cell, electrode layers with superposed alignment layers on the insides of the outer plates, a tilt angle between the longitudinal axis of the molecules at the surface of the outer plates and the outer plates of from about 1 degree to 30 degrees, and a twist angle of the liquid-crystal mixture in the cell from alignment layer to alignment layer with a value of between 100 and 600°, a nematic liquid-crystal mixture consisting of
a) 20–90% by weight of a liquid-crystalline component A consisting of one or more compounds having a dielectric anisotropy of greater than +1.5;
b) 10–65% by weight of a liquid-crystalline component B consisting of one or more compounds having a dielectric anisotropy of between −1.5 and +1.5;
c) 0–20% by weight of a liquid-crystalline component D consisting of one or more compounds having a dielectric anisotropy of below −1.5, and
d) an optically active component C in an amount that the ratio between the layer thickness (separation of the plane-parallel outer plates) and the natural pitch of the chiral nematic liquid-crystal mixture is from about 0.2 to 1.3, characterized in that component B comprises at least one compound of the formula I

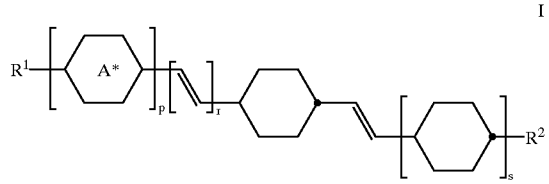

I in which

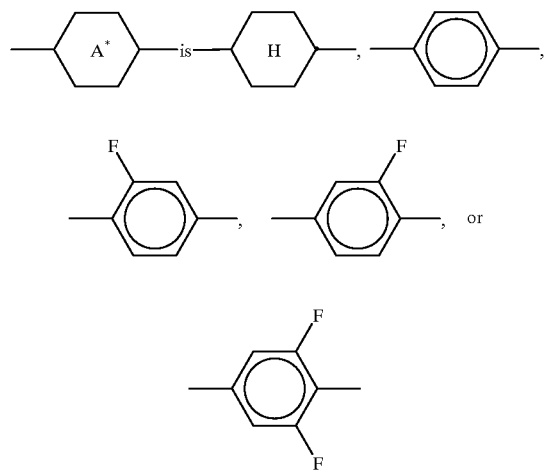

$R^1$ is an alkyl, alkoxy or alkenyl radical having 1 to 10 carbon atoms which is unsubstituted or monosubstituted by CN or $CF_2$ or at least monosubstituted by halogen, it also being possible for one or more $CH_2$ groups in this radical to be replaced by —O—, $R^2$ is $(CH_2)_n$—CH=CH—$R^a$ or $(CH_2)_n$—CH=$CH_2$, and, in the case where r=1, $R^a$ alternatively $R^a$ is a straight-chain alkyl having 1–6 carbon atoms, n is 0–6, p and r are each, independently of one another, 0 or 1, and s is 1 or 2.

The invention also relates to corresponding liquid-crystal mixtures for use in SLCDs.

Preferred compounds of the formula I are in particular compounds of the subformulae IA to IK ($L^1$ and $L^2$=H or F; n=0–6; o=0–6; alkyl=$C_{1-6}$)

IA

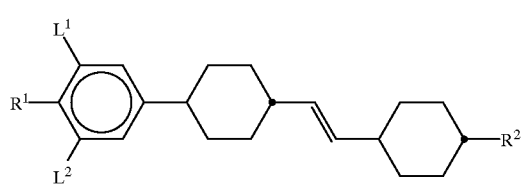

IB

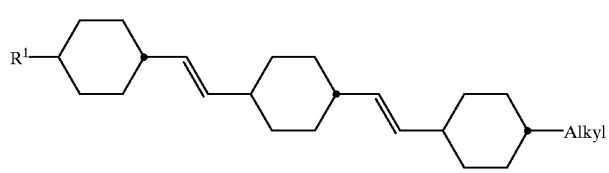

-continued
IC
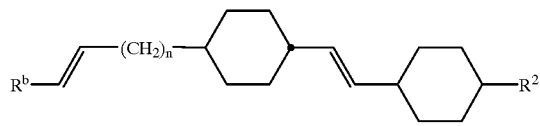
ID
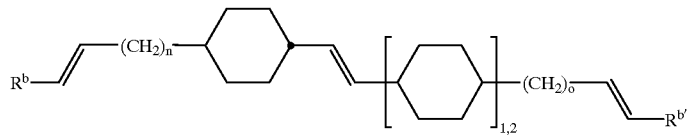
IE
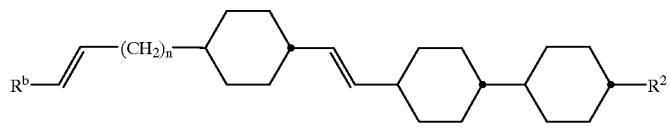
IF
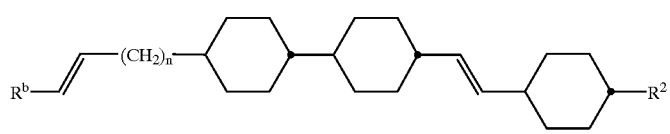
IG
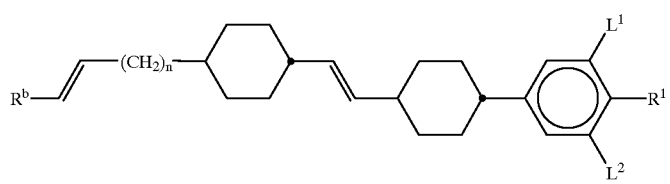
IH
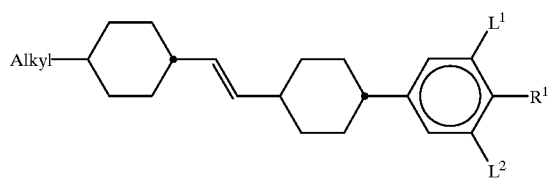
II
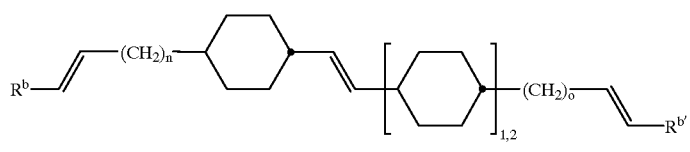
IJ
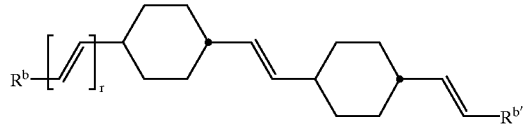
IK
Preferred novel mixtures comprising, in particular, compounds of the subformulae I1–I8:

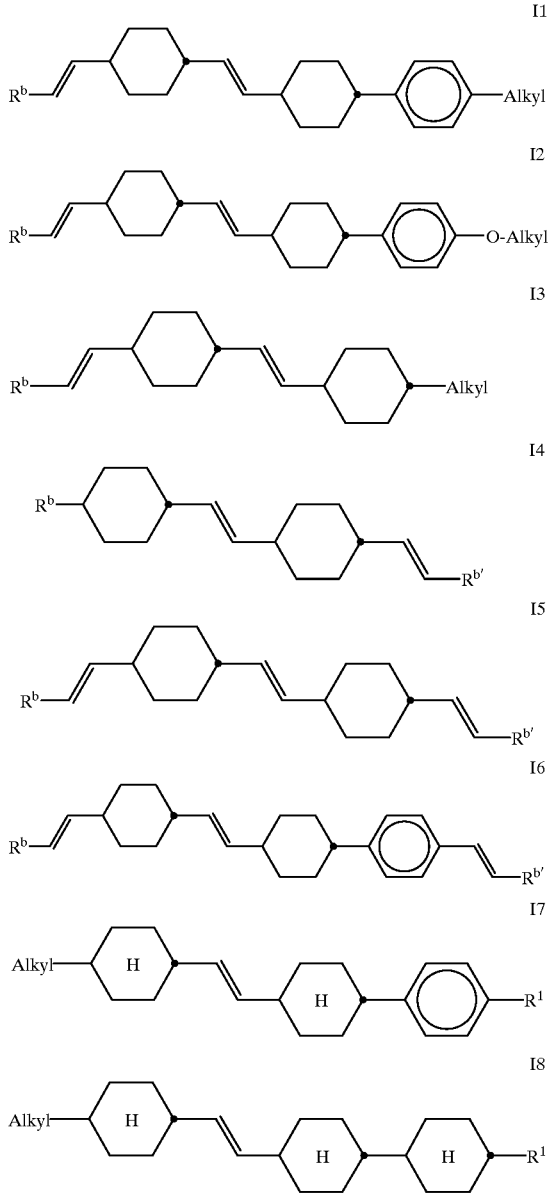

$R^a$ is preferably straight-chain alkyl, and n is 0–6. $R^b$ and $R^{b'}$, independently of one another in the subformulae IC–IJ, are each preferably H or methyl, furthermore ethyl, propyl, butyl, pentyl or hexyl. o is from 0 to 6.

In the compounds of the formula I, $R^1$ is preferably alkyl, alkoxy, CN or a halogenated alkyl or alkenyl radical. Halogen is preferably F. $R^1$ is, in particular, F, Cl, $OCF_3$, $OCF_2H$, $CF_3$, $OCH_2CF_3$, $OCHFCF_3$, $OC_2F_5$, $C_2F_5$, $OC_2F_4H$ or $OCHF_2$, if p=1, and the ring A* is

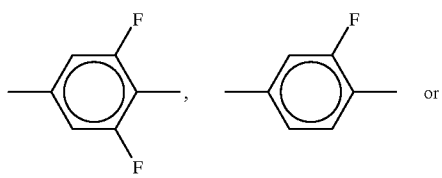

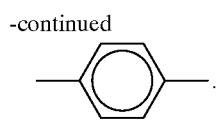

Particular preference is given to compounds in which $R^1$ and/or $R^2$ are an alkenyl radical, in which the double bond is in the 1- or 3-position and has the trans-configuration.

If $R^1$ is an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, methoxy, octoxy, nonoxy or decoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkyl radical in which one $CH_2$ group has been replaced by —CH=CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one $CH_2$ group has been replaced by —O— and one has been replaced by —CO—, these are preferably adjacent. These thus contain one acyloxy group —CO—O— or one oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ is an alkyl radical in which one $CH_2$ group has been replaced by unsubstituted or substituted —CH=CH— and an adjacent $CH_2$ group has been replaced by CO or CO—O or O—CO, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl and 9-methacryloyloxynonyl.

If $R^1$ is an alkyl or alkenyl radical which is monosubstituted by CN or $CF_3$, this radical is preferably straight-chain and the substitution by CN or $CF_3$ is in the ω-position.

If $R^1$ is an alkyl or alkenyl radical which is at least monosubstituted by halogen, this radical is preferably straight-chain and halogen is preferably F or Cl. In the case of multiple substitution, halogen is preferably F. The resultant radicals also include perfluorinated radicals. In the case of monosubstitution, the fluorine or chlorine substituent can be in any desired position, but is preferably in the ω-position.

Compounds of the formula I containing branched wing groups $R^1$ may occasionally be of importance due to better solubility in the customary liquid-crystalline base materials, but in particular as chiral dopes if they are optically active.

Branched groups of this type generally contain not more than one chain branch. Preferred branched radicals are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

If $R^1$ is an alkyl radical in which two or more $CH_2$ groups have been replaced by —O— and/or —CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis-(methoxycarbonyl)butyl, 5,5-bis(methoxycarbonyl)pentyl, 6,6-bis(methoxycarbonyl)hexyl, 7,7-bis(methoxycarbonyl)-heptyl, 8,8-bis(methoxycarbonyl)octyl, bis(ethoxycarbonyl) methyl, 2,2-bis(ethoxycarbonyl)ethyl, 3,3-bis (ethoxycarbonyl)propyl, 4,4-bis(ethoxycarbonyl)butyl and 5,5-bis(ethoxycarbonyl)hexyl.

Compounds of the formula I which contain wing groups $R^1$ which are suitable for polycondensation reactions are suitable for the preparation of liquid-crystalline polycondensates.

The formula I covers the racemates of these compounds and the optical antipodes, and mixtures thereof.

Of these compounds of the formula I and the subformulae, preference is given to those in which at least one of the radicals present therein has one of the preferred meanings indicated.

In the compounds of the formula I, preference is given to the stereoisomers in which the cyclohexane rings are trans-1,4-disubstituted.

The compounds of the formula I are prepared by methods known per se, as described in the literature (for example in the standard works such as Houben-Weyl, Methoden der Organischen Chemie, Georg-Thieme-Verlag, Stuttgart), to be precise under reaction conditions which are known and are suitable for said reactions.

The novel compounds are prepared, for example, as described in DE 35 09 170 A1:

Scheme 1

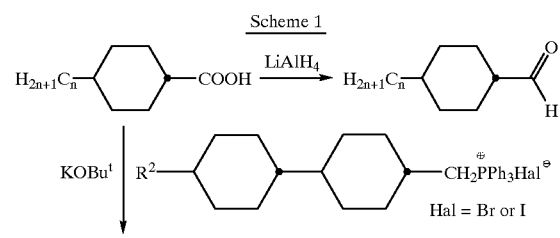

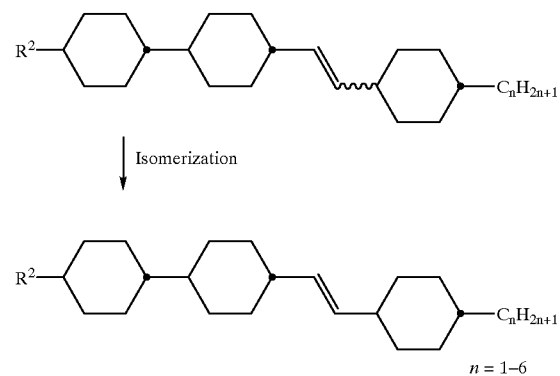

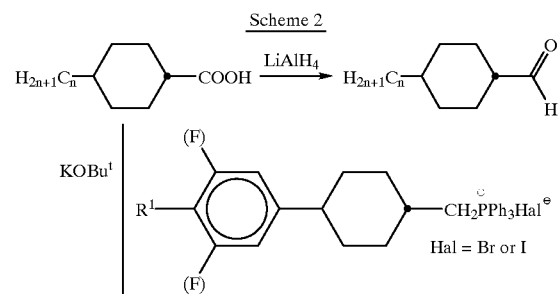

Scheme 2

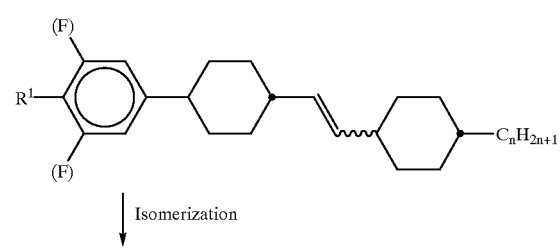

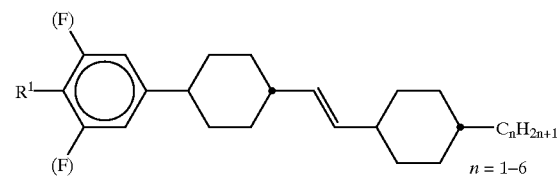

6,017,469
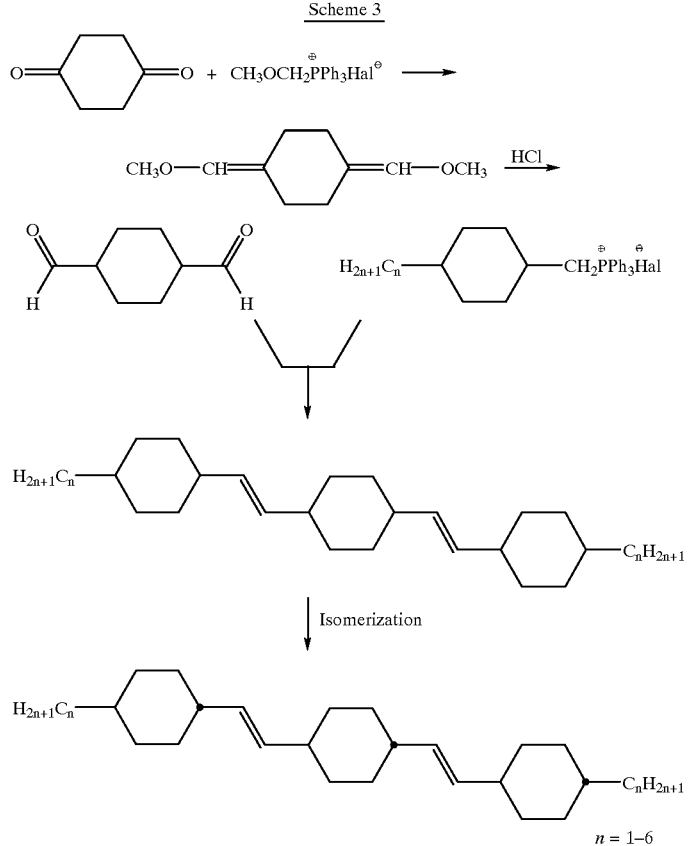
The novel compounds can furthermore be prepared as follows; use can also be made here of variants which are known per se, but are not described here in greater detail.
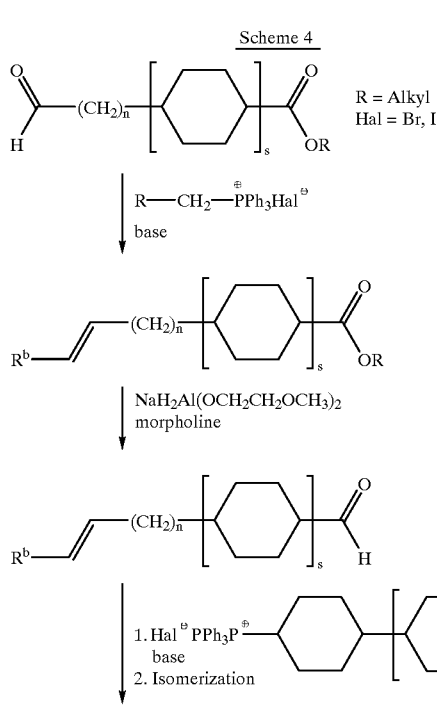
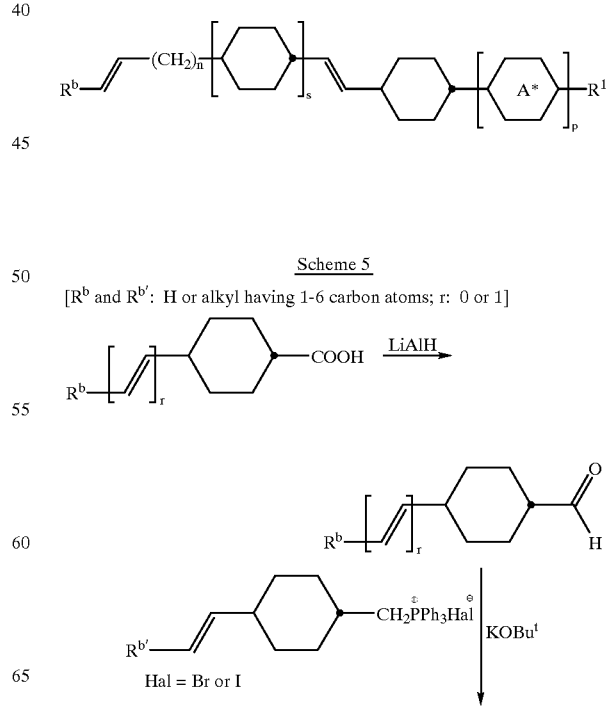
Scheme 5
[$R^b$ and $R^{b'}$: H or alkyl having 1-6 carbon atoms; r: 0 or 1]

Scheme 6

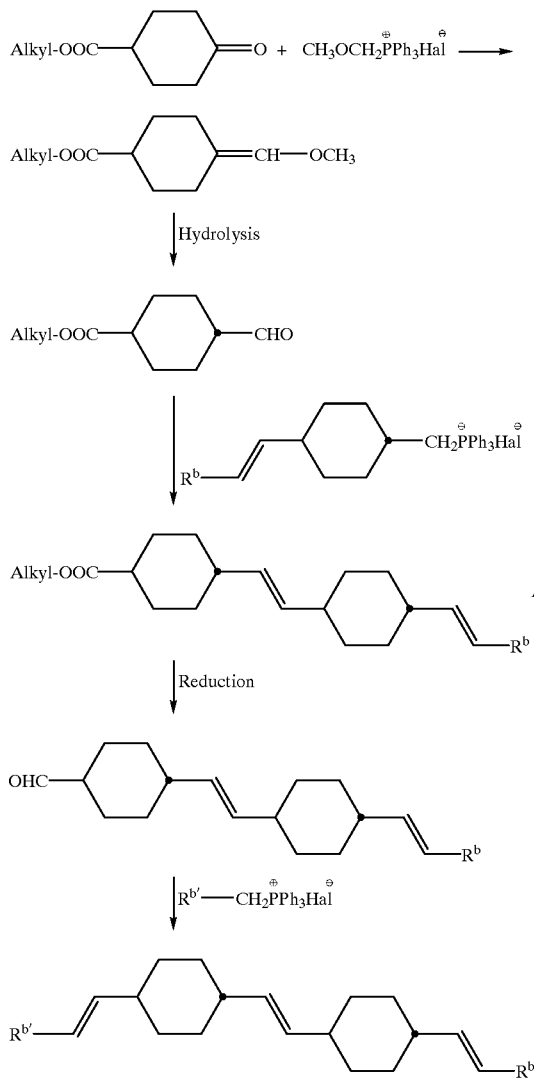

The invention likewise relates to a process for the preparation of the compounds of the formulae I4, I5 and the novel intermediates of the formula A.

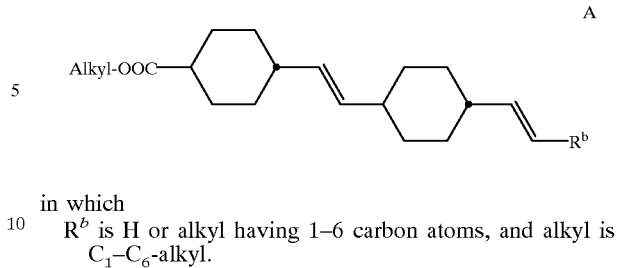

in which
$R^b$ is H or alkyl having 1–6 carbon atoms, and alkyl is $C_1$–$C_6$-alkyl.

Scheme 7

[$R^b$ and $R^{b'}$: H or alkyl]

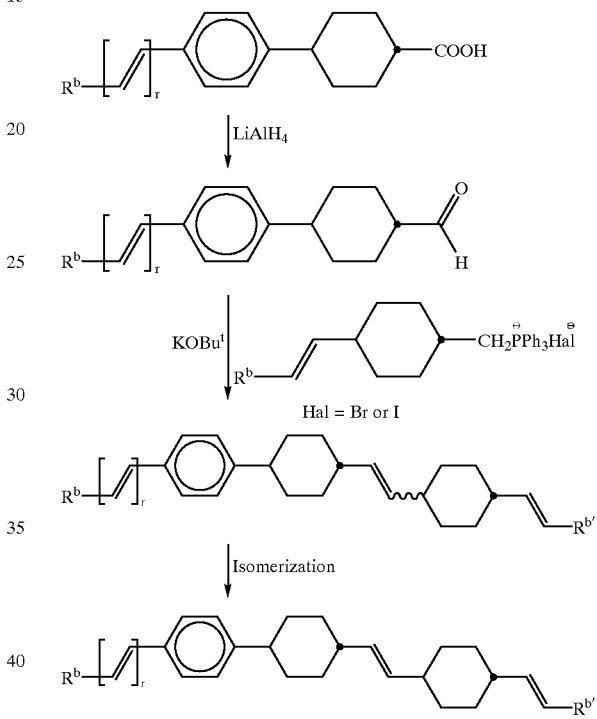

The novel liquid-crystal mixtures preferably have the following composition:

Component A preferably comprises compounds of the formulae II and III

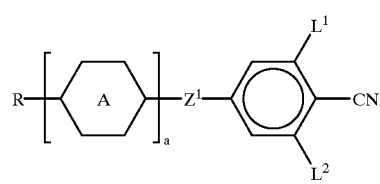

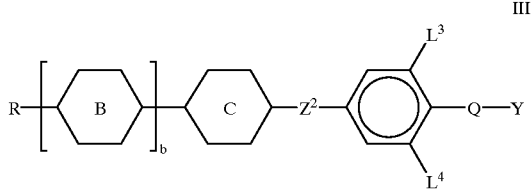

in which

R is an alkyl group having 1 to 12 carbon atoms, it also being possible for one or two non-adjacent CH₂ groups to be replaced by —O—, —CH=CH—, —CO—, —OCO— or —COO—,

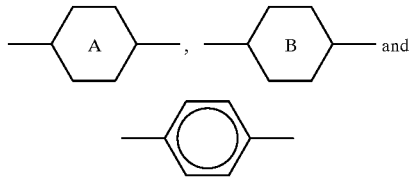

is each, independently of one another,

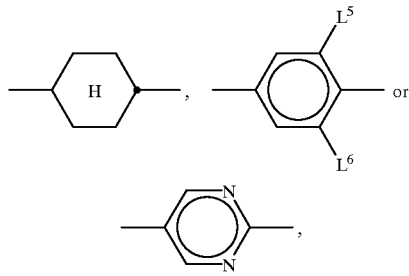

$L^{1-6}$ are each, independently of one another, H or F, $Z^1$ is —COO—, —CH₂CH₂— or a single bond, $Z^2$ is —CH₂CH₂—, —COO—, —C≡C— or a single bond, Q is —CF₂—, —CHF—, —OCF₂—, —OCHF— or a single bond, Y is F or Cl, a is 1 or 2, and b is 0 or 1.

Preferred compounds of the formula II conform to the subformulae IIa to IId:

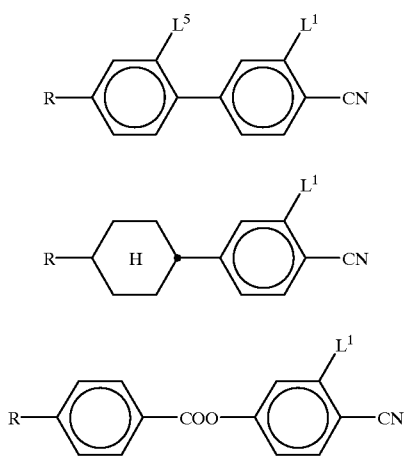

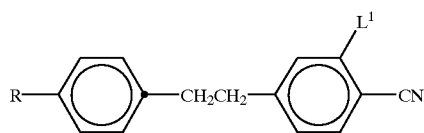

where R, $L^1$ and $L^5$ are as defined above.

Preferred compounds of the formula III conform to the subformulae IIIa–IIIt:

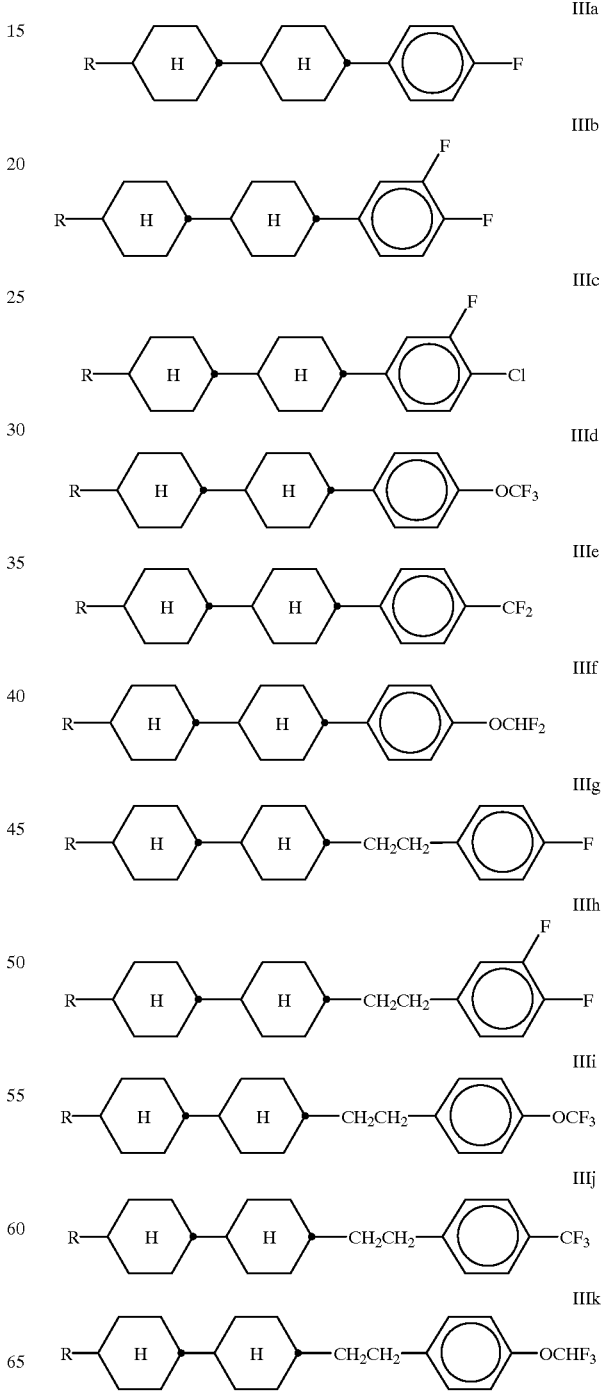

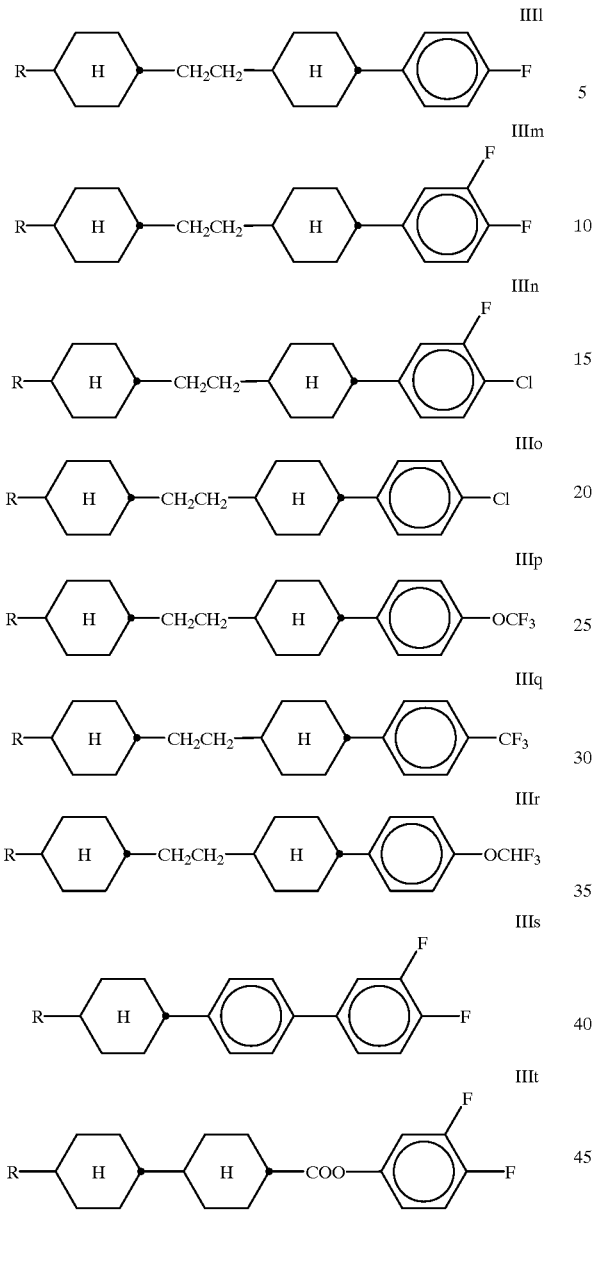

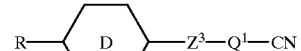

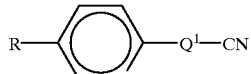

In addition to one or more compounds of the formula I, preferred mixtures comprise one, two, three, or more compounds of the formulae IIa, IIb, IIc, IId, IIId, IIIh, IIIi, IIIl, IIIm or IIIs, preferably one or more compounds of the formula IIId or IIIh, and one to four compounds of the formula I and one to three compounds of the formulae IIb and IIc.

The individual compounds, for example, of the formulae II and III or their subformulae or alternatively other compounds which can be used in the novel SLCDs are either known or can be prepared analogously to the known compounds.

In a particularly preferred embodiment, component A additionally comprises compounds of the formulae AI to AV:

in which

R is an alkyl group having 1 to 12 carbon atoms, it also being possible for one or two non-adjacent $CH_2$ groups to be replaced by —O—, —CH=CH—, —CO—, —OCO— or —COO—, $Q^1$ is

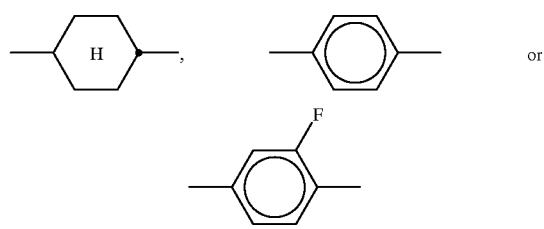

$Z^3$ is

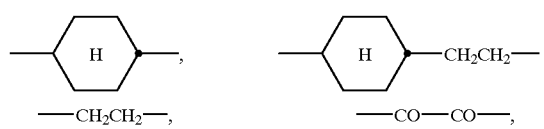

—CO— or a single bond, and

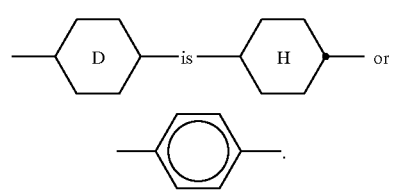

The mixtures preferably comprise from 5 to 50% of compounds of the formula AI. Prefence is given to the compounds of the formula AI in which $Z^1$ is —$CH_2CH_2$—, —COO— or a single bond, in particular compounds of the formulae IIa1, IIb1, IIc1, IId1, IIa2, IIb2 and IIc2:

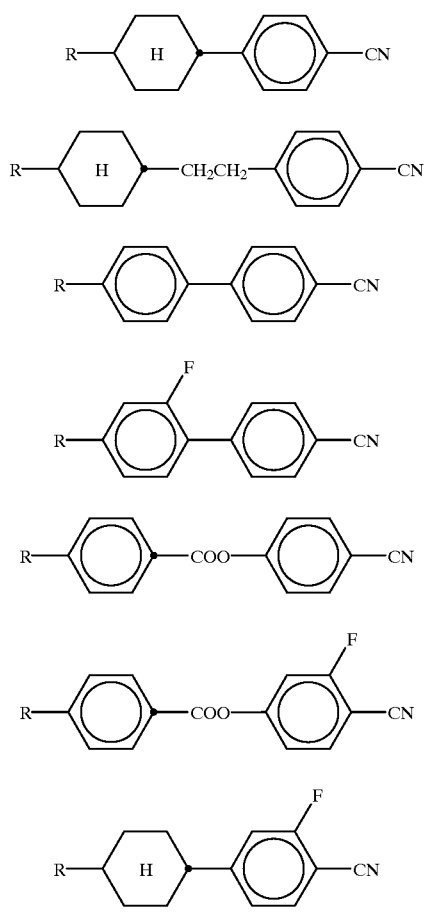

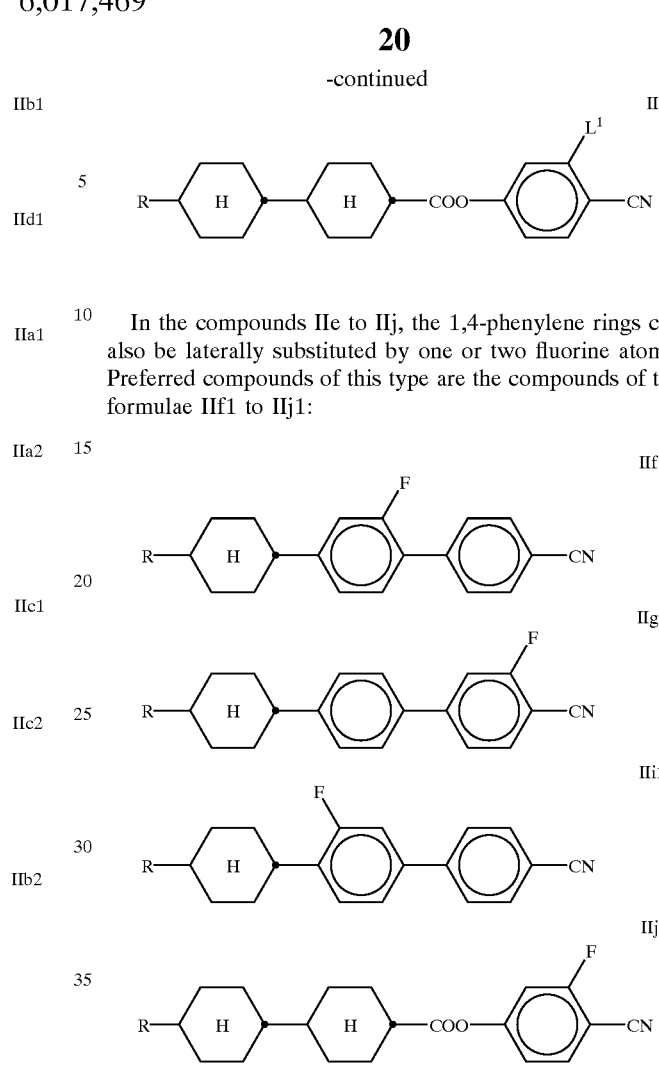

Component A preferably comprises one or more compounds of the formulae IIb1 and, if desired, one or more compounds of the formulae IIc2.

The novel mixtures preferably comprise one or more polar compounds having a high clearing point selected from the group consisting of the compounds IIe to IIj:

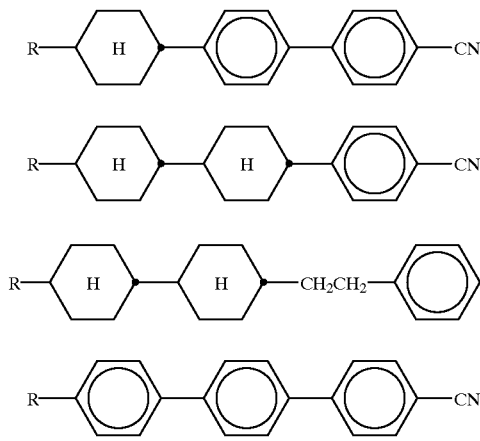

In the compounds IIe to IIj, the 1,4-phenylene rings can also be laterally substituted by one or two fluorine atoms. Preferred compounds of this type are the compounds of the formulae IIf1 to IIj1:

In the novel mixtures, the proportion of compounds IIe to IIj is preferably from about 2 to 25%. Preferred liquid-crystal mixtures comprise one or more compounds from Group B, preferably 10 to 40%.

The compounds from the group B are distinguished both by their low rotational viscosity ($\gamma_1$) values of <150 mpa·s and by their high clearing point (>120° C.).

Component B comprises one or more compounds selected from the group consisting of the compounds of the formulae IV1 to IV9:

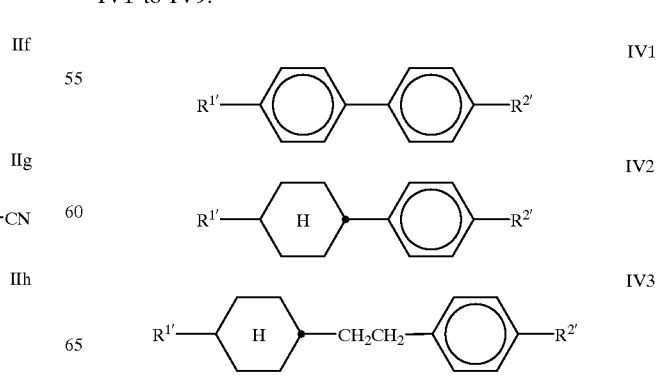

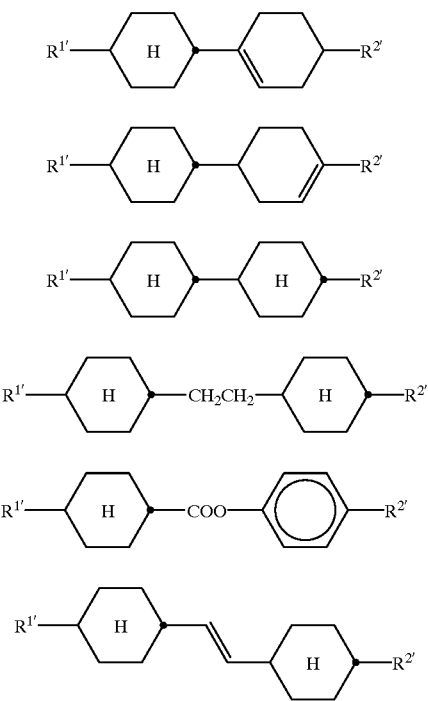

in which $R^1$ and $R^2$ are as defined for R.

Component B additionally comprises one or more compounds selected from the group consisting of the compounds of the formulae IV10 to IV24

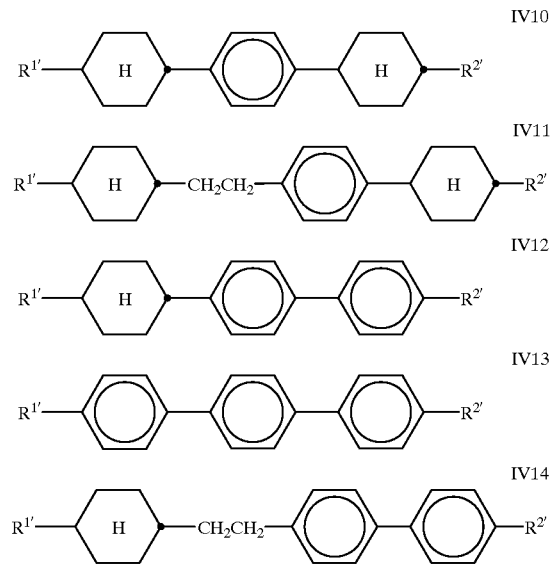

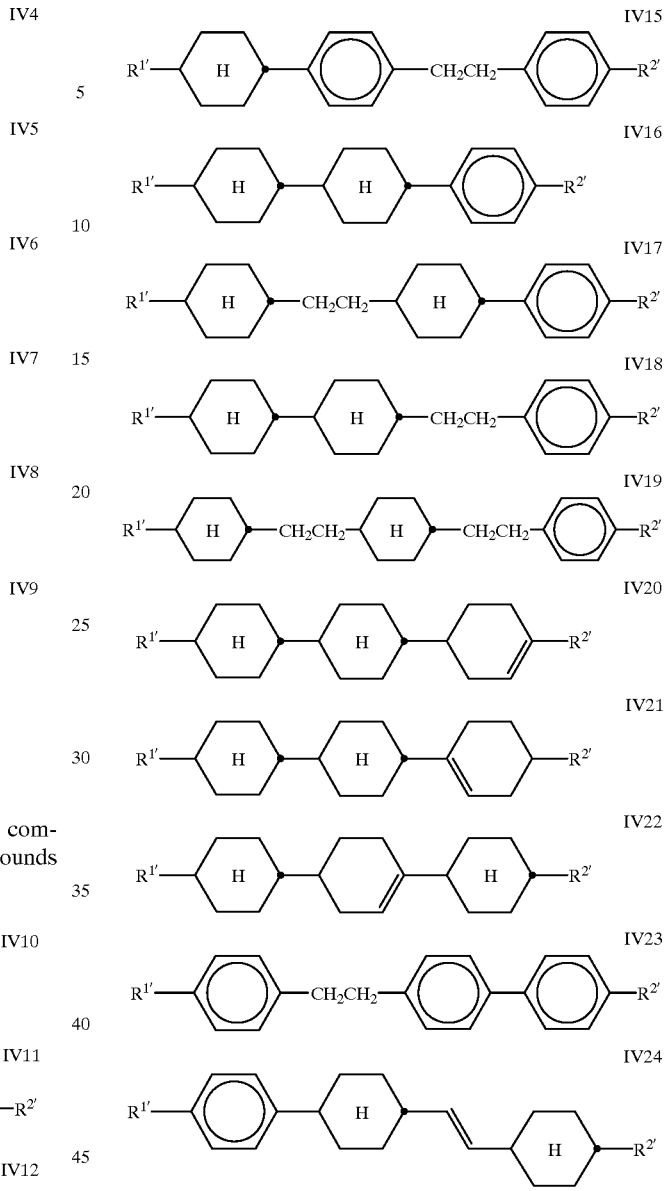

in which $R^{1'}$ and $R^{2'}$ are as defined for R, and the 1,4-phenylene groups in IV10 to IV19, IV23 and IV24 may each, independently of one another, also be monosubstituted or polysubstituted by fluorine.

Component B additionally comprises one or more compounds selected from the group consisting of the compounds of the formulae IV25 to IV30

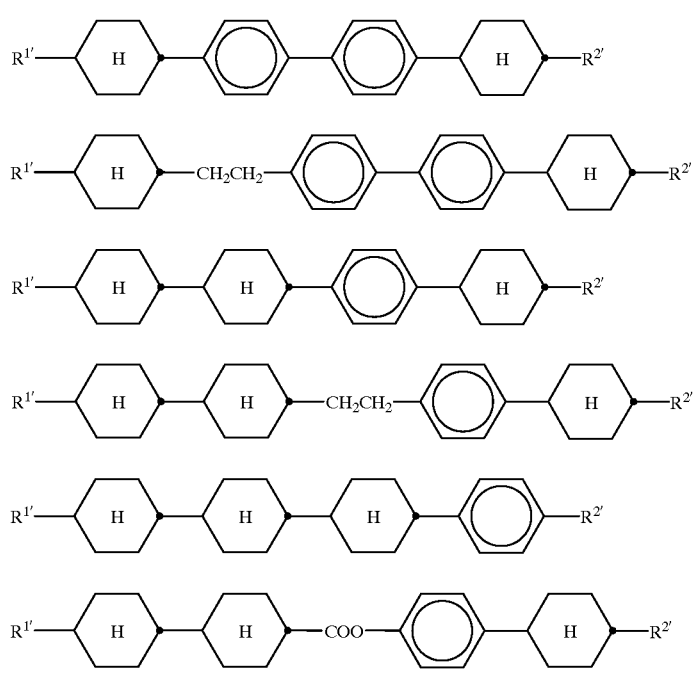

IV25

IV26

IV27

IV28

IV29

IV30 in which $R^{1'}$ and $R^{2'}$ are as defined for R, and the 1,4-phenylene groups in IV25 to IV30 may also each, independently of one another, be monosubstituted or polysubstituted by fluorine.

Component B comprises one or more compounds selected from the group consisting of IV31 and IV32:

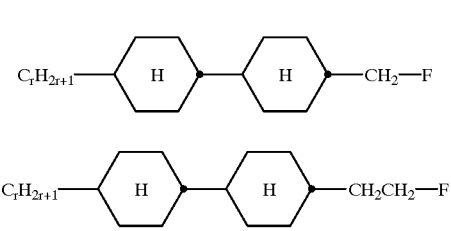

IV31

IV32 in which $C_rH_{2r+1}$ is a straight-chain alkyl group having up to 9 carbon atoms.

In addition to components A, B and C, the liquid-crystal mixture additionally comprises one or more compounds selected from the group consisting of the compounds of the formulae III and IV, in which $R^1$ and $R^2$ are as defined for R:

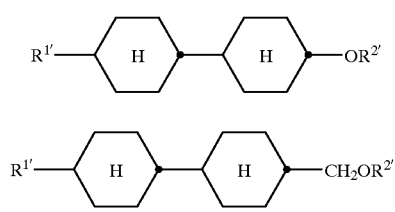

III

IV

Preferred liquid-crystal mixtures comprise at least one component selected from the group consisting of the following compounds:

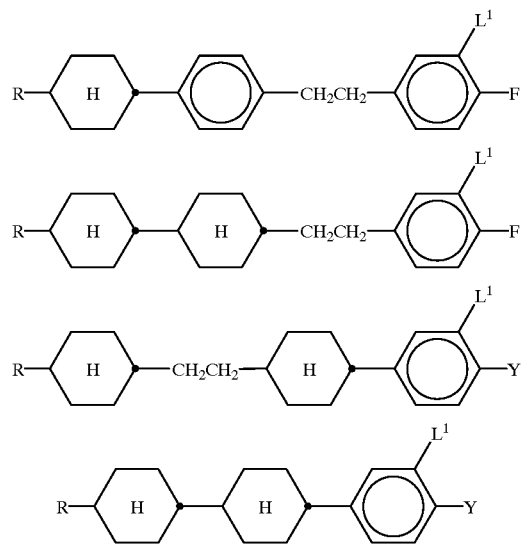

in which Y is F or Cl, and $L^1$ is H or F, and R is as defined above.

The liquid-crystal mixtures likewise comprise an optically active component C in such an amount that the ratio between the layer thickness (separation of the plane-parallel outer plates) and the natural pitch of the chiral nematic liquid-crystal mixture is greater than 0.2. For the component, a multiplicity of chiral dopes, some commercially available, is available to the person skilled in the art, for example such as cholesteryl nonanoate, S811 from E. Merck, Darmstadt, FRG, and CB 15 (BDH, Poole, UK). The choice of dopes is not crucial per se.

The novel liquid-crystal mixture preferably comprises one or more compounds selected from Group B1 consisting of compounds of the formulae B1I to B1IV:

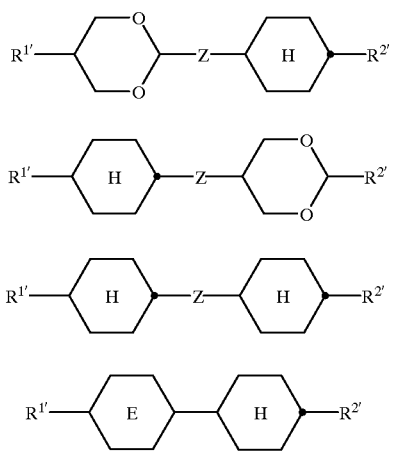

in which

R$^{1'}$ and R$^{2'}$ are each, independently of one another, as defined for R,

Z is —CH$_2$CH$_2$—, —CO—O—, —O—CO— or a single bond, and

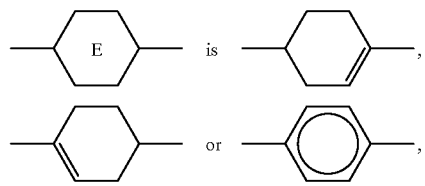

and/or at least one compound selected from Group B2 consisting of compounds of the formulae B1V to B1VII:

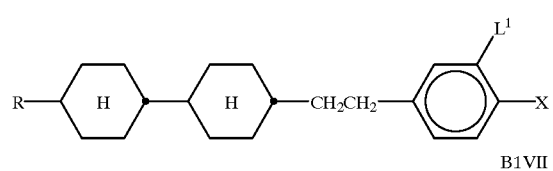

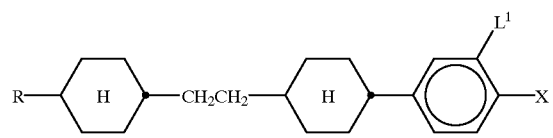

in which

R is as defined above,

Z$^o$ is —CH$_2$CH$_2$— or a single bond,

Q$^o$ is

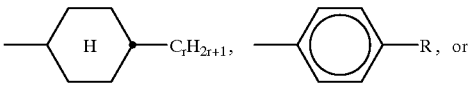

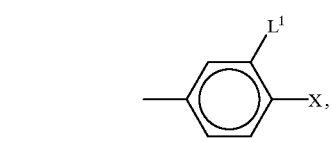

where r is 1–9,

X is CN or F,

L$^1$ is H or F, and/or at least one compound selected from Group B3 consisting of compounds of the formulae B1VIII, B1IX and B1X:

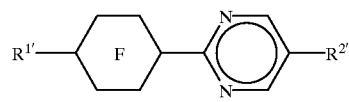

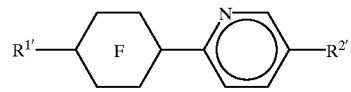

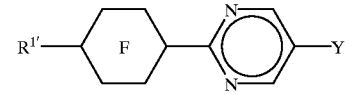

in which

R$^{1'}$ and R$^{2'}$, independently of one another, are as defined for R,

Y is F or Cl, and

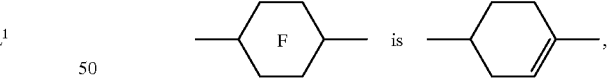

In a particularly preferred embodiment, the novel mixtures comprise from about 5 to 35%, in particular from 10 to 20%, of liquid-crystalline tolan compounds. This enables smaller layer thicknesses (about 5–6 µm) to be used, significantly shortening the response times. Particular preference is given to mixtures comprising one or more compounds selected from Group T consisting of the compounds of the formulae T1 to T3:

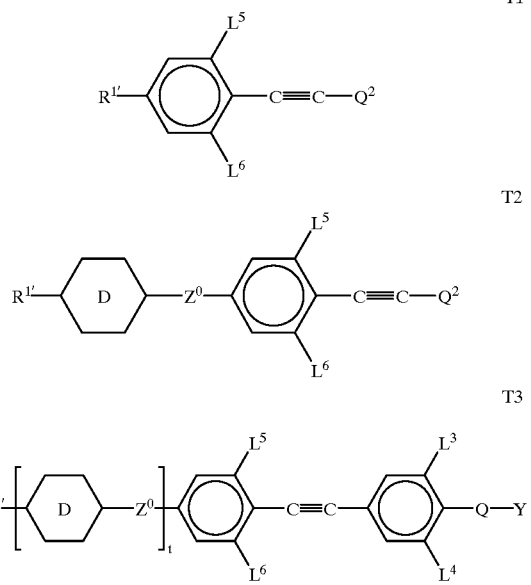

T1

T2

T3 in which

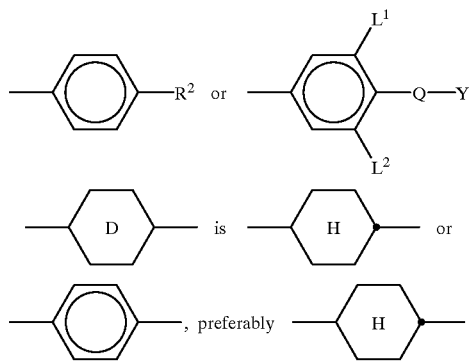

t is 0 or 1

$L^{1-6}$ are each, independently of one another, H or F

Q is —$CF_2$—, —CHF—, —$OCF_2$—, —OCHF— or a single bond

Y is F or Cl $R^{1'}$ and $R^{2'}$ are each, independently of one another, as defined for R.

The proportion of compounds from the group T is preferably from 5 to 30%, in particular from 5 to 20%.

Component B preferably comprises one or more compounds of the formulae X to XII:

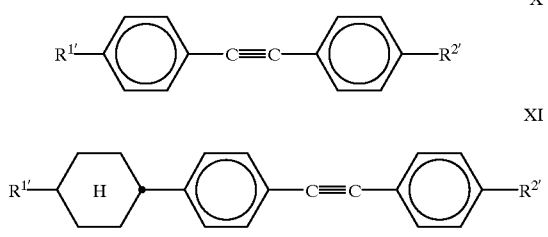

X

XI

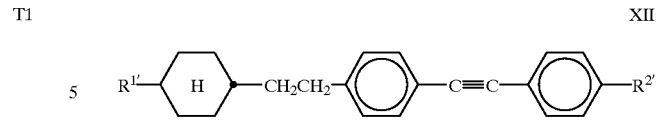

XII in which $R^{1'}$ and $R^{2'}$ are each, independently of one another, as defined for R, and $R^{1'}$ is preferably alkyl having 1 to 4 carbon atoms, in particular 1 to 2 carbon atoms, and $R^{2'}$ is preferably alkoxy having 1 to 4 carbon atoms, in particular 1 to 2 carbon atoms.

The proportion of compounds from group B1 is preferably from 10 to 50%, in particular from 15 to 40%. Compounds of the formula B1III and B2IV are preferred.

Particularly preferred compounds of the formula B1III are those of the following subformulae B1IIIa and B1IIIb

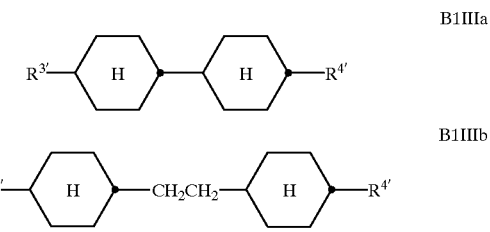

B1IIIa

B1IIIb in which $R^{3'}$ is $CH_3$—$(CH_2)_o$—O—, $CH_3$—$(CH_2)_p$—, trans—H—$(CH_2)_q$—CH=CH—$(CH_2CH_2)_b$—$CH_2$O— or trans—H—$(CH_2)_q$—CH=CH—$(CH_2CH_2)_b$—, $CH_3$—$(CH_2)_o$—O—$CH_2$—, $R^{4'}$ is $CH_3$—$(CH_2)_p$—, o is 1, 2, 3 or 4, q is 0, 1, 2 or 3, b is 0 or 1, and p is 1, 2, 3 or 4.

Particular preference is given to compounds of the formula B1III, in which one of the radicals $R^{3'}$ or $R^{4'}$ is O—$(CH_2)_o$—$CH_3$ or $CH_2$—O—$(CH_2)_o$—$CH_2$—.

Preference is furthermore given to the compounds of the subformula

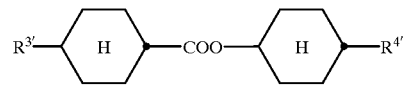

in which $R^{3'}$ and $R^{4'}$ are each, independently of one another, as defined above.

The proportion of compounds of the formula B1III of the abovementioned subformulae is preferably from about 5 to 45%, particularly preferably from about 10% to 35%. Particularly preferred compounds of the formula B1IV are those of the following subformula

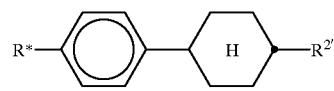

in which

R* is $CH_3$—$(CH_2)_o$—O— or trans—H—$(CH_2)_q$—CH=CH—$(CH_2CH_2)_b$—$CH_2$—, and $R^{2'}$ is $CH_3—(CH_2)_p—$, where o is 1, 2, 3 or 4, q is 0, 1, 2 or 3, b is 0 or 1, and p is 1, 2, 3 or 4.

The proportion of these compounds or of compounds of the formula BIV is preferably from about 5 to 40%, particularly preferably from about 10 to 35%.

The mixtures preferably comprise compounds of the formula B1III, in particular those of the subformula

In a particularly preferred embodiment, the mixtures simultaneously comprise compounds of the formulae B1III and B1IV, where the total proportion of components from group B1 remains observed.

If compounds of the formulae B1I and/or B1III are present, $R^2$ and $R^3$ are preferably each, independently of one another, n-alkyl having 1 to 7 carbon atoms or (trans)-n-alkenyl having 3 to 7 carbon atoms. Z is preferably a single bond.

Preference is furthermore given to novel mixtures which comprise one or more compounds of the formula B1IV in which

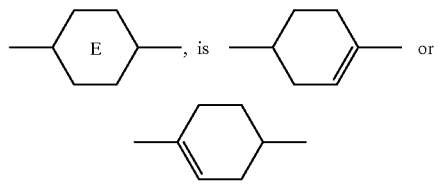

$R^{1'}$ and $R^{2'}$ have one of the preferred meanings given above, particularly preferably n-alkyl having 1 to 7 carbon atoms.

In all cases, the total proportion of components from group B1 remains observed.

The proportion of compounds from group B2 is preferably from about 5 to 45%, in particular from 5 to 20%. The proportion (preferred ranges) for B1V to B1VII is as follows:

B1IV: from about 5 to 30%, preferably from about 5 to 15%

Sum of B1VI and B1VII: from about 5 to 25%, preferably from about 10 to 20%.

Preferred compounds from group B2 are shown below:

B1V1

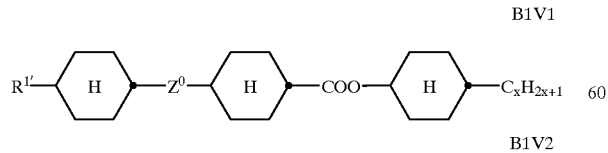

B1V2

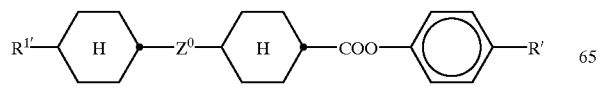

-continued

B1V3

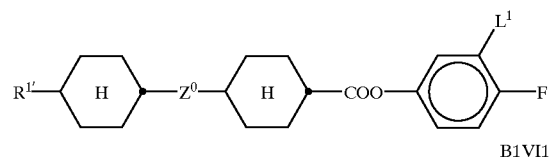

B1VI1

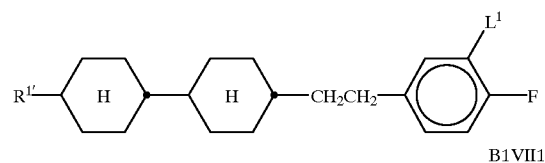

B1VII1

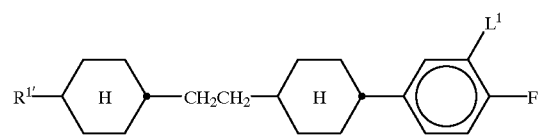

R' is preferably n-alkyl having 1 to 7 carbon atoms or (trans)-n-alkenyl having 3 to 7 carbon atoms. $Z^0$ is preferably a single bond. $R^{1'}$ preferably has the preferred meaning given above for R or is fluorine. $L^1$ is preferably fluorine. x is 1–15.

The novel mixtures preferably comprise one or more compounds selected from the group consisting of B1V3, B1VI1 and B1VII1 in a total proportion of from about 5 to 35%.

In a particularly preferred embodiment, the novel mixtures, in addition to B1V3, B1VI1 and B1VII1 (R=F), comprise further terminally fluorinated compounds selected, for example, from the group consisting of

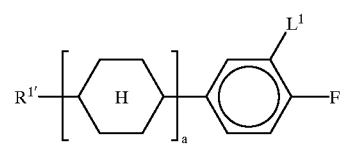

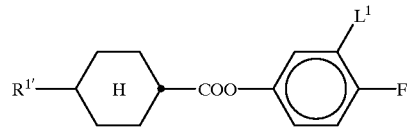

and/or polar heterocyclic compounds selected from the group consisting of

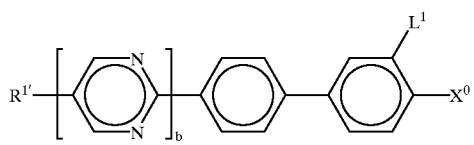

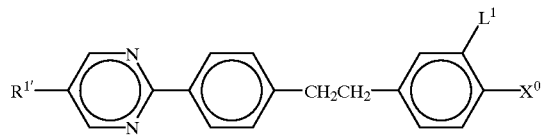

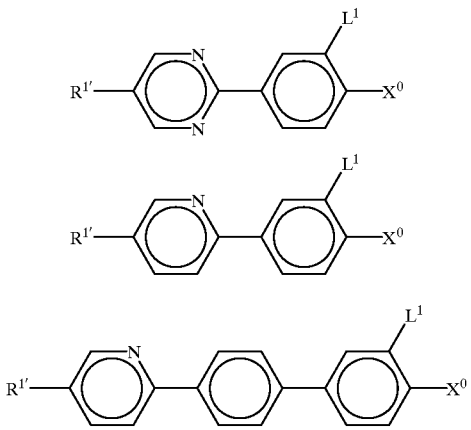

in which $R^{1'}$ is preferably n-alkyl having 1 to 7 carbon atoms or (trans)-n-alkenyl having 3 to 7 carbon atoms, a is 1 or 2, b is 0 or 1, $X^o$ is F, Cl, $CF_3$, —$OCF_3$ or —$OCHF_3$, and $L^1$ is H or F.

The total proportion of all terminally fluorinated compounds is preferably from about 5 to 65%, in particular from about 15 to 40%.

The proportion of compounds from group B3 is preferably from about 5 to 30%, particularly preferably from about 10 to 20%. $R^{2'}$ is preferably n-alkyl or n-alkoxy, in each case having 1 to 9 carbon atoms.

However, it is also possible to use analogous compounds containing alkenyl or alkenyloxy groups. Compounds of the formula B1VIII are preferred.

The novel mixtures preferably comprise compounds of the formula I and compounds from at least one of groups B1, B2 and B3. They preferably comprise one or more compounds from group B1 and one or more compounds from group B2 and/or B3.

The proportion of compounds of component C is preferably from 0 to 20%, in particular from 0 to 10%.

In a particularly preferred embodiment, the novel mixtures preferably comprise from about 5 to 20% of one or more compounds having a dielectric anisotropy of below –2 (component C). Compounds of this type are known, for example derivatives of 2,3-dicyanohydroquinones or cyclohexane derivatives containing the structural unit

as described in DE-A 32 32 707 or DE-A 34 07 013.

However, preference is given to compounds containing the structural unit 2,3-difluoro-1,4-phenylene, for examples compounds as described in DE-A 38 07 801, 38 07 861, 38 07 863, 38 07 864 or 38 07 908. Particular preference is given to tolans containing this structural unit, as described in International Patent Application PCT/DE 88/00133, in particular those of the formulae

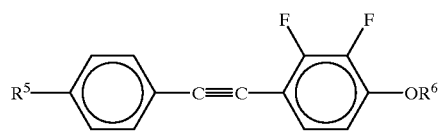

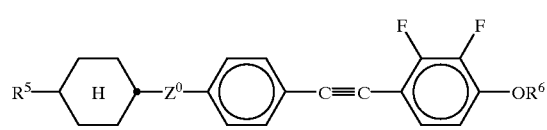

in which $R^5$ and $R^6$ are each, independently of one another, preferably n-alkyl having 1 to 7 carbon atoms or n-alkenyl having 3 to 7 carbon atoms, and $Z^0$ is —$CH_2CH_2$— or a single bond.

Particular preference is given to phenyl cyclohexylcarbxylates of the formulae

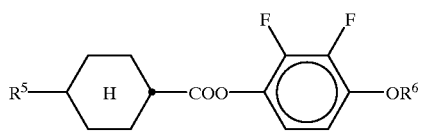

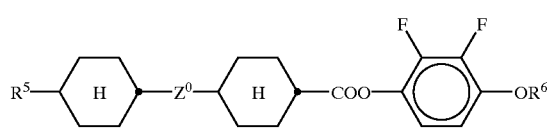

Component C comprises one or more compounds selected from the group consisting of V to IX:

V

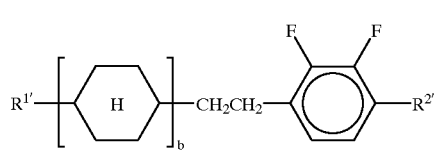

VI

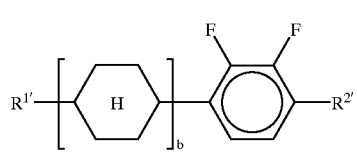

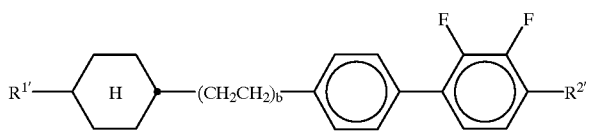
VII

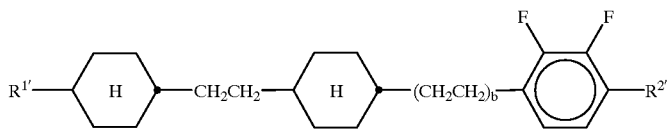
VIII

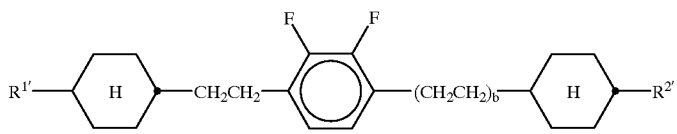
IX in which $R^{1'}$ and $R^{2'}$ are as defined for R, and b is 0 or 1.

Component B comprises one or more compounds selected from the group consisting of Xa to XIIa

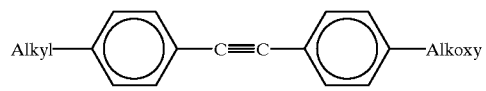
Xa

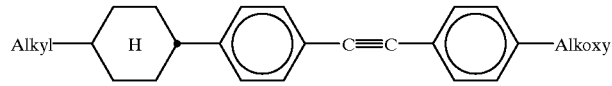
XIa

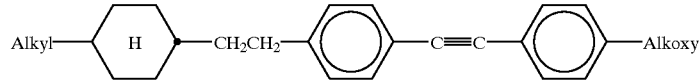
XIIa in which alkyl and alkoxy are an alkyl or alkoxy radical having 1 to 7 carbon atoms.

Component C in particular results in an increased steepness of the characteristic line.

In a particularly preferred embodiment, the mixtures comprise from about 5 to 35%, particularly preferably from about 10 to 20%, of liquid-crystalline tolan compounds. This allows smaller layer thicknesses (about 5–6 μm) to be used, significantly shortening the response times. Particularly preferred tolans are shown below:

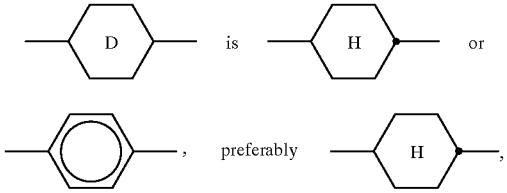

T1a

T2a $R^{1*}$ is preferably n-alkyl or n-alkoxy having 1 to 7 carbon atoms, $Z^0$ is —CH$_2$CH$_2$— or a single bond, D is H or preferably H, $Q^3$ is —R$^{2'}$, —X$^0$ or —F—X, where X⁰ is F, Cl or OCF₃, where R²* is n-alkyl or n-alkoxy, in each case having 1 to 7 carbon atoms, or n-alkenyl or n-alkenyloxy, in each case having 3 to 7 carbon atoms.

Component A preferably comprises one or more compounds of the formula T3a

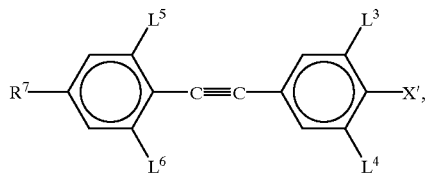

T3a in which

R⁷ is —$C_xH_{2x+1}$,

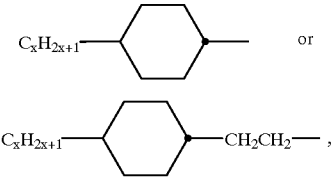

x is an integer from 1 to 15, $L^{3-6}$ are each, independently of one another, H or F, and X' is F, Cl or OCF₃.

Further particularly preferred embodiments are given below:

Component C comprises one or more compounds containing a 1-cyano-trans-1,4-cyclohexyl group or a 2,3-difluro-1,4-phenylene group at least two compounds of the formulae AIII or AV compounds of the formulae AIII and AV at least one compound from the group consisting of:

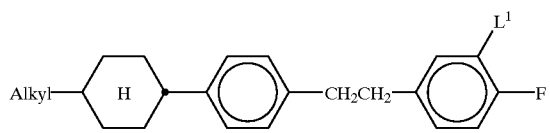

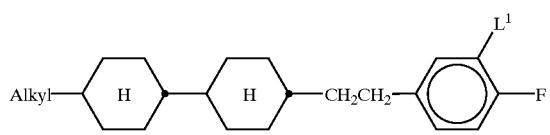

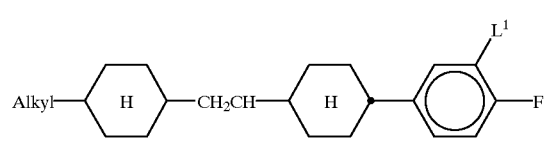

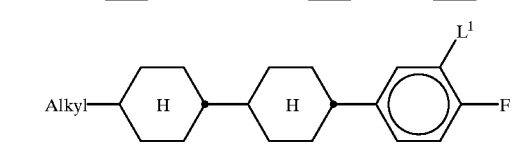

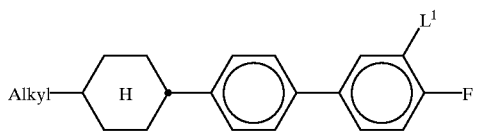

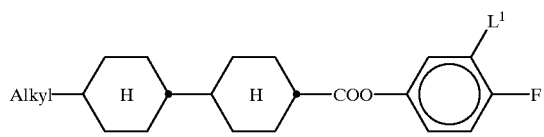

in which Alkyl is a straight-chain alkyl radical having 2 to 7 carbon atoms, and L¹ is H or F;

one or more compounds in which R is a trans-alkenyl group or a trans-alkenyloxy group;

one or more compounds selected from the following group:

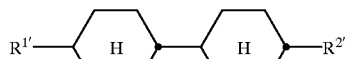

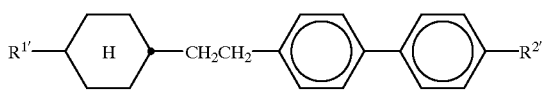

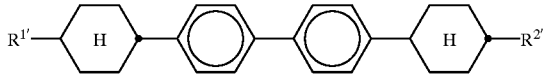

in which R²' and R²' have the preferred meanings given under compounds of component B. The 1,4-phenylene group in the abovementioned compounds can also be substituted by fluorine. The proportion of these compounds in the liquid-crystal mixtures is-from 0 to 25%, preferably from 5 to 15%.

In a further preferred embodiment, the mixtures comprise
one or more, in particular 1, 2, 3 or 4, compounds selected from the compounds of the formulae IIId, IIIb, IIi and IIIp;
at least two compounds selected from the compounds of the formulae IIb1, IIb1 or IIc2;
one or more compounds of the formula B1IV;
one or more compounds of the formula T1 or T2;
one or more compounds of the formulae

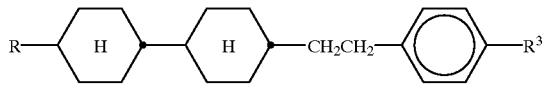

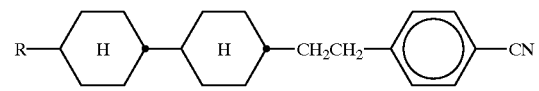

in which R is as defined under the formula III.

In particular when used in SLCDs having high layer thicknesses, the novel mixtures are distinguished by very low overall response times (=$t_{on}+t_{off}$).

Low overall response times are an important criterion, in particular, in SLCDs for use as displays in laptops in order to be able to display curser movements without interference.

The liquid-crystal mixtures used in the SLCDs according to the invention are dielectrically positive with $\Delta\epsilon \geq 1$. Particular preference is given to liquid-crystal mixtures where $\Delta\epsilon$ is $\geq 3$ and very particularly to those where $\Delta\epsilon$ is $\geq 5$.

The liquid-crystal mixtures according to the invention have favorable values for the threshold voltage $V_{10/0/20}$ and for the flow viscosity $\eta$. If the value for the optical path difference $d.\Delta n$ is specified, the value for the layer thickness d is determined by the optical anisotropy $\Delta n$. In particular at relatively high values for $d.\Delta n$, the use of liquid-crystal mixtures according to the invention having a relatively high value for the optical anisotropy is generally preferred since the value for d can then be chosen to be relatively small, which results in more favorable values for the response times. However, liquid-crystal displays according to the invention which contain liquid-crystal mixtures according to the invention having relatively small values for $\Delta n$ are also characterized by advantageous values for the response times. The liquid-crystal mixtures according to the invention are furthermore characterized by advantageous values for the steepness of the electrooptical characteristic line and can be operated at high multiplex rates. In addition, the liquid-crystal mixtures according to the invention have high stability and favorable values for the electrical resistance and the frequency dependence of the threshold voltage. The liquid-crystal displays according to the invention have a broad operating temperature range and good angle dependence of the contrast.

The construction of the liquid-crystal display elements according to the invention from polarisers, electrode base plates and electrodes with a surface treatment such that the preferential alignment (director) of the liquid-crystal molecules in each case adjacent thereto is usually twisted by a value of from 160° to 720° from one electrode to the next, corresponds to the structure which is conventional for display elements of this type. The term conventional structure here is broadly drawn and also includes all derivatives and modifications of the supertwist cell, in particular also matrix display elements, and display elements which contain additional magnets. The surface tilt angle at the two outer plates may be identical or different. Identical tilt angles are preferred.

An essential difference of the display elements according to the invention to those customary hitherto based on the twisted nematic cell is, however, the choice of the liquid-crystal components of the liquid-crystal layer.

The liquid-crystal mixtures which can be used according to the invention are prepared in a manner which is known per se. In general, the desired amount of the components used in a lesser amount is dissolved in the components making up the principal constituent, expediently at elevated temperature. It is also possible to mix solutions of the components in an organic solvent, for example in acetone, chloroform or methanol, and, after mixing, to remove the solvent again, for example by distillation.

The dielectrics may also contain further additives which are known to a person skilled in the art and are described in the literature. For example, 0–15% of pleochroic dyes may be added.

The examples below are intended to illustrate the invention without representing a limitation.

The following abbreviations are used:

S-N smectic-nematic phase transition temperature,

N-I nematic-isotropic phase transition temperature, c.p. clearing point, visc. viscosity (mPa.s), $t_{on}$ time from switching on until 90% of the maximum contrast is achieved, $t_{off}$ time from switching off until 10% of the maximum contrast is achieved.

$V_{90}/V_{10}$ steepness $$t_{ave} = \frac{t_{on} + t_{off}}{2} \quad \text{(average response time)}$$

The SLCD is operated in multiplex mode (multiplex ratio) 1:240, bias 1:16, operating voltage 10 volts, so that $t_{on}=t_{off}$.

Above and below, all temperatures are indicated in °C. The percentages are per cent by weight. The values for the response times and viscosities relate to 20° C.

In the present application and in the examples below, the structures of the liquid-crystal compounds are indicated by acronyms, the transformation into chemical formulae taking place in accordance with tables A and B below. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is given. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nmF | $C_nH_{2n+1}$ | $C_mH_{2m+1}$ | F | H |
| $nCF_3$ | $C_nH_{2n+1}$ | $CF_3$ | H | H |
| $nOCF_3$ | $C_nH_{2n+1}$ | $OCF_3$ | H | H |
| $nOCF_2$ | $C_nH_{2n+1}$ | $OCHF_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nNF | $C_nH_{2n+1}$ | CN | F | H |
| nAm | $C_nH_{2n+1}$ | $COOC_mH_{2m+1}$ | H | H |
| nF.Cl | $C_nH_{2n+1}$ | Cl | H | F |

In addition to one or more compounds of the formula I, preferred mixtures comprise one or more of the compounds mentioned in Tables A and B.

TABLE A
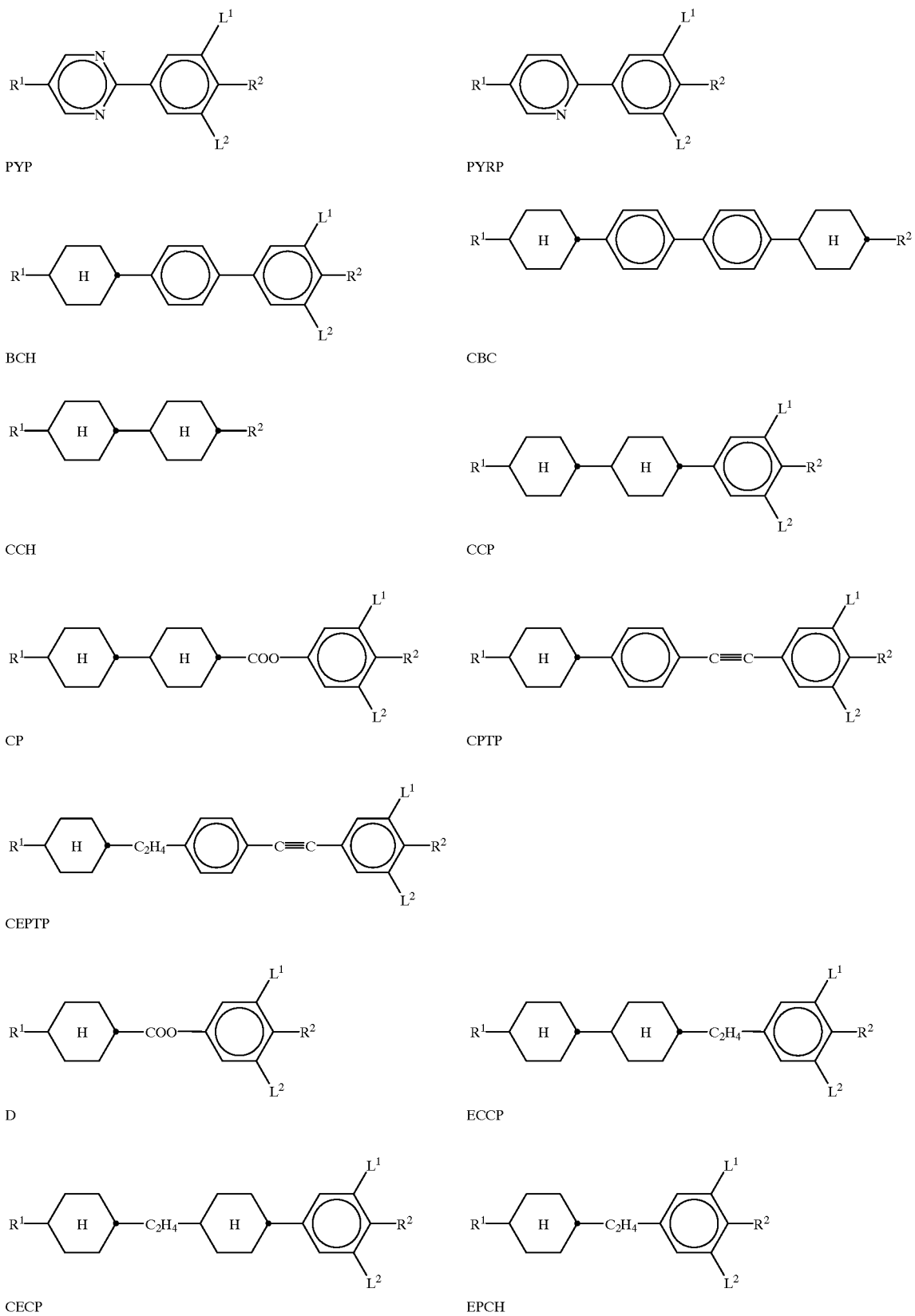

TABLE A-continued
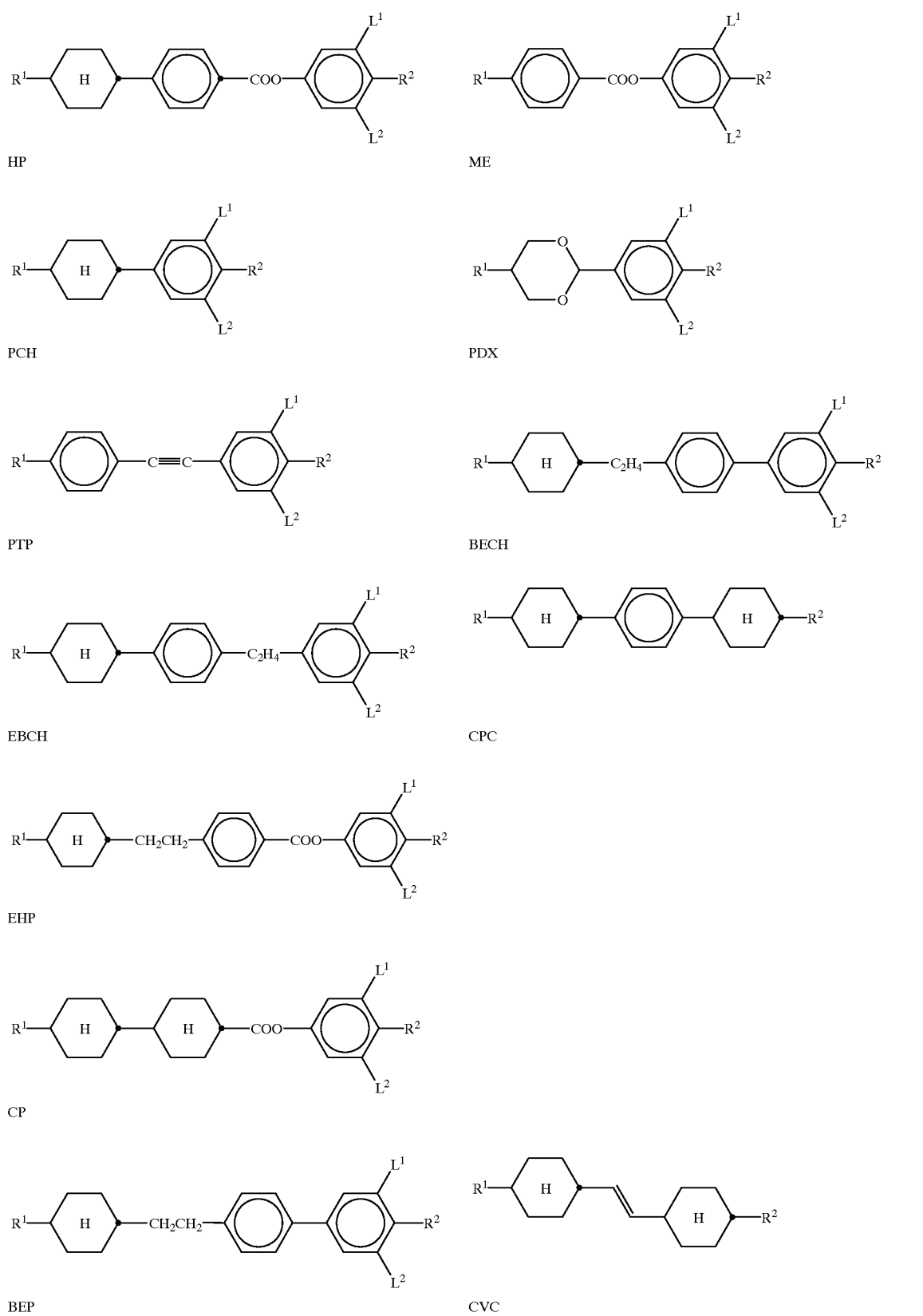

TABLE A-continued
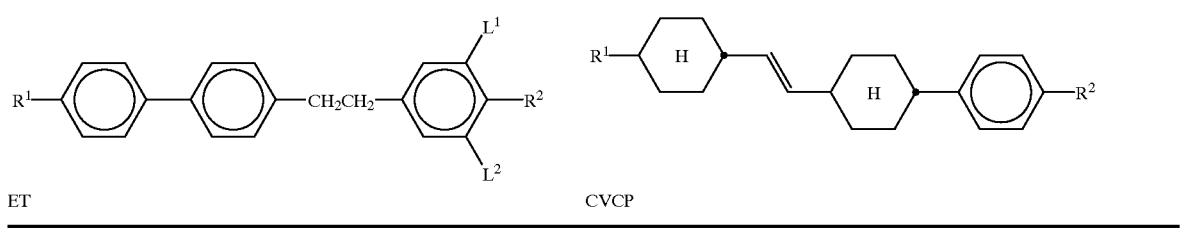
ET  CVCP
TABLE B
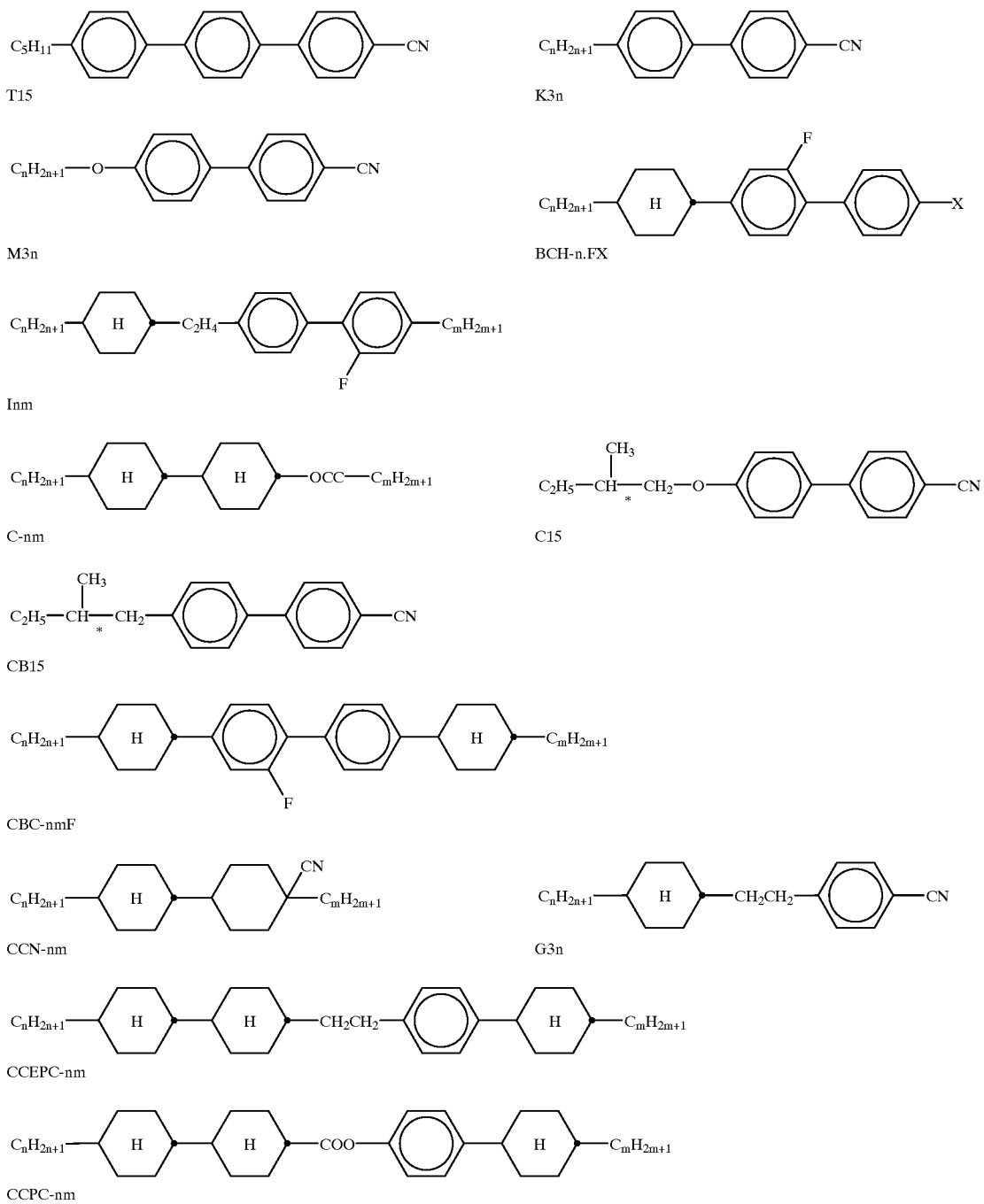

TABLE B-continued $C_nH_{2n+1}$—[H]—[H]—COO—[H]—$C_mH_{2m+1}$

CH-nm $C_nH_{2n+1}$—[H]—[⌬]—OOC—[H]—$C_mH_{2m+1}$

HD-nm $C_nH_{2n+1}$—[H]—[⌬]—COO—[H]—$C_mH_{2m+1}$

HH-nm $C_nH_{2n+1}$—[⌬]—[⌬]—[H]$\begin{smallmatrix}CN\\C_mH_{2m+1}\end{smallmatrix}$ NCB-nm $C_nH_{2n+1}$—[H]—COO—[H]—$C_mH_{2m+1}$ OS-nm $C_2H_5$—[H]—COO—[⌬]—[⌬]—CN

CHE $C_nH_{2n+1}$—[H]—$C_2H_4$—[⌬]—[⌬]—[H]—$C_mH_{2m+1}$

ECBC-nm $C_nH_{2n+1}$—[H]—$C_2H_4$—[H]—$C_mH_{2m+1}$

ECCH-nm $C_nH_{2n+1}$—[H]—[H]—$CH_2O$—$C_mH_{2m+1}$

CCH-n1EM $C_nH_{2n+1}$—[⌬]—[⌬]$_F$—[⌬]—CN

T-nFN $C_nH_{2n+1}O$—[⌬]—[⌬]$_F$—CN

B-nO.FN $C_nH_{2n+1}$—[H]—CH=CH—[H]—[H]—$C_mH_{2m+1}$

CVCC-n-m $C_nH_{2n+1}$—[H]—CH=CH—[H]—[⌬]—$C_mH_{2m+1}$

CVCP-n-m

TABLE B-continued
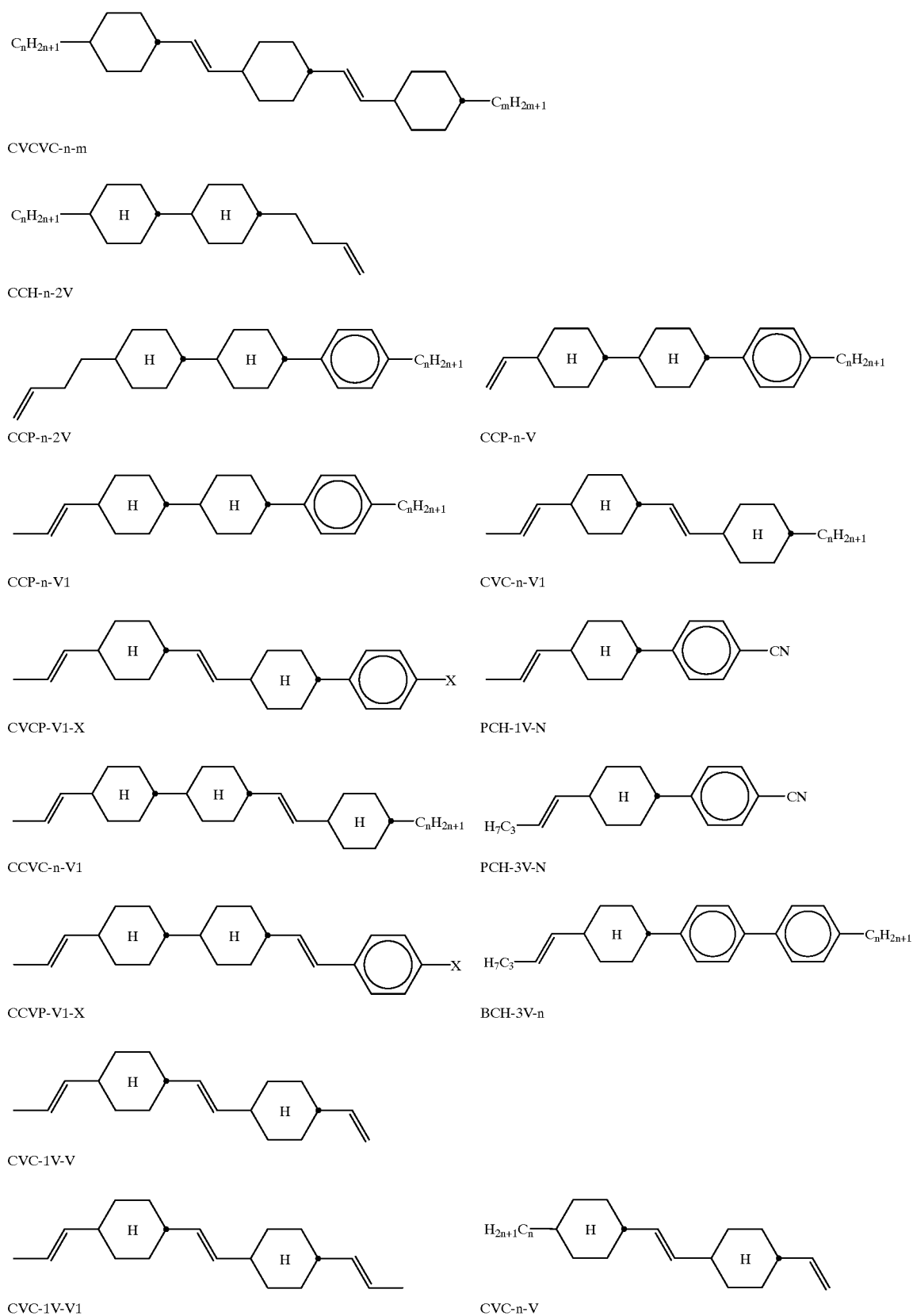

TABLE B-continued

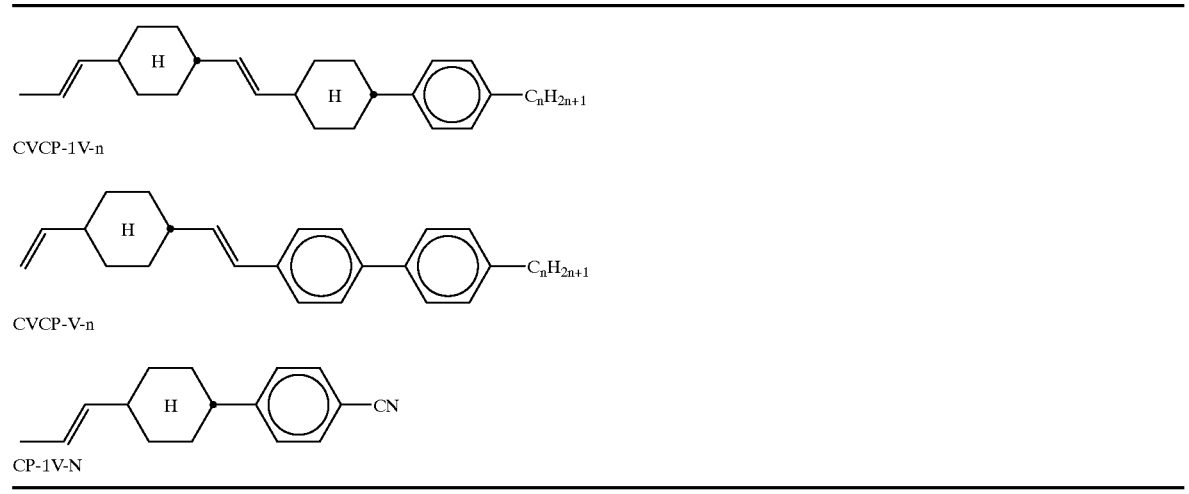

CVCP-1V-n

CVCP-V-n

CP-1V-N

The examples below are intended to illustrate the invention without representing a limitation. Above and below, percentages are per cent by weight. All temperatures are given in degrees Celcius. m.p. denotes melting point, c.p.= clearing point. Furthermore, C=crystalline state, N=nematic phase, S=smectic phase and I=isotropic phase. The numbers between these symbols represent the transition temperatures. $\Delta n$ denotes optical anisotropy (589 nm, 20° C.), and the viscosity (mm$^2$/sec) was determined at 20° C.

"Conventional work-up" means that water is added if necessary, the mixture is extracted with dichloromethane, diethyl ether, methyl tert-butyl ether or toluene, the organic phase is separated off, dried and evaporated, and the product is purified by distillation under reduced pressure or crystallization and/or chromatography. The following abbreviations are used:

DAST Diethylaminosulfur trifluoride
DMEU 1,3-dimethyl-2-imidazolidinone
POT Potassium tert-butoxide
THF Tetrahydrofuran
pTsOH p-toluenesulfonic acid

EXAMPLE 1

Step 1.1

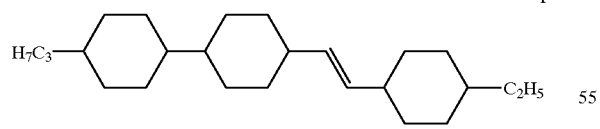

Under a nitrogen atmosphere, 0.4 mol of trans-4-n-ethylcyclohexylmethyltriphenylphosphonium iodide and 0.4 mol of 4-[trans-4-(trans-4-propylcyclohexyl)cyclohexanecarbaldehyde are dissolved in 1140 ml of THF, and 0.4 mol of potassium tert-butoxide is added at room temperature with stirring. The mixture is stirred overnight at room temperature, water and dilute hydrochloric acid are added, and the mixture is subjected to conventional work-up.

Step 1.2

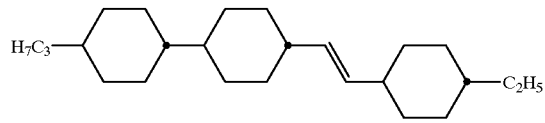

0.275 mol of I are dissolved in 400 ml of toluene under a nitrogen atmosphere, and the mixture is refluxed with 0.072 mol of sodium benzenesulfinate and 110 ml of 1 N hydrochloric acid. The mixture is subsequently subjected to conventional work-up.

The following compounds of the formula

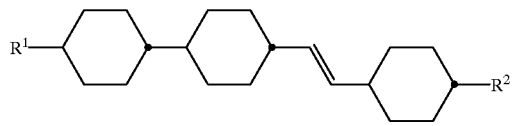

are prepared analogously:

| $R^1$ | $R^2$ | |
|---|---|---|
| $CH_3$ | $CH_3$ | |
| $CH_3$ | $C_2H_5$ | |
| $CH_3$ | n-$C_3H_7$ | |
| $CH_3$ | n-$C_5H_{11}$ | |
| $CH_3$ | n-$C_6H_{13}$ | |
| $C_2H_5$ | $CH_3$ | C? −23 $S_M$51 $S_B$ 168 N 170, 1 I; $\Delta \epsilon$ = 0.6, $\Delta n$ = + 0.068 |
| $C_2H_5$ | $C_2H_5$ | C −11 $S_B$ 183 N 188.8 I; $\Delta \epsilon$ = 0.41; $\Delta n$ = + 0.078 |
| $C_2H_5$ | n-$C_3H_7$ | C? −15 $S_B$ 184 N 207.3 I; $\Delta[$ = 0.85; $\Delta n$ = +0.080 |
| $C_2H_5$ | n-$C_5H_{11}$ | |
| $C_2H_5$ | n-$C_6H_{13}$ | |
| n-$C_3H_7$ | $CH_3$ | C? −19 $S_M$ 16 $S_B$ 188 N 197.4 I; $\Delta \epsilon$ = −1.06; $\Delta n$ = 0.085 |
| n-$C_3H_7$ | $C_2H_5$ | C −28 $S_B$ 197 N 207.9 I; $\Delta n$ = +0.078; $\Delta \epsilon$ = 0.88 |
| n-$C_3H_7$ | n-$C_3H_7$ | C 39 $S_B$ 207 N 231.8 I; $\Delta n$ = +0.087; $\Delta \epsilon$ = 0.99 |
| n-$C_3H_7$ | n-$C_5H_{11}$ | |
| n-$C_3H_7$ | n-$C_6H_{13}$ | |

-continued

| $R^1$ | $R^2$ |
|---|---|
| n-C$_5$H$_{11}$ | CH$_3$ |
| n-C$_5$H$_{11}$ | C$_2$H$_5$ |
| n-C$_5$H$_{11}$ | n-C$_3$H$_7$ |
| n-C$_5$H$_{11}$ | n-C$_5$H$_{11}$ |
| n-C$_5$H$_{11}$ | n-C$_6$H$_{13}$ |

EXAMPLE 2

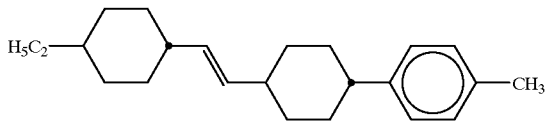

Step 2.1

Under a nitrogen atmosphere, 162 mmol of trans-4-n-ethylcyclohexylethyltriphenylphosphonium bromide and 162 mmol of trans-4-(4-methylphenyl)cyclohexanecarbaldehyde are dissolved in 500 ml of THF, and 162 mmol of potassium tert-butoxide are added at room temperature with stirring. The mixture is stirred for 2 hours, water is added, and the mixture is subjected to conventional work-up.

Step 2.2

The isomerization is carried out analogously to Step 1.2.
C 43 S$_B$ 89 N 156.6 I; Δn=+0.103; Δε=0.58
The following compounds of the formula

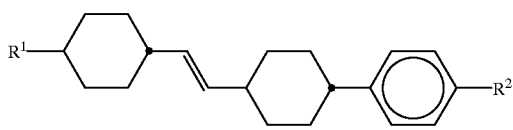

are prepared analogously:

| $R^1$ | $R^2$ | |
|---|---|---|
| CH$_3$ | CH$_3$ | C 77 N 141.9 I; Δn = +0.114; Δε = 0.76 |
| CH$_3$ | C$_2$H$_5$ | |
| CH$_3$ | n-C$_3$H$_7$ | |
| CH$_3$ | n-C$_5$H$_{11}$ | |
| CH$_3$ | n-C$_6$H$_{13}$ | |
| C$_2$H$_5$ | CH$_3$ | C 43 S$_B$ 89 N 157 I |
| C$_2$H$_5$ | C$_2$H$_5$ | |
| C$_2$H$_5$ | n-C$_3$H$_7$ | |
| C$_2$H$_5$ | n-C$_5$H$_{11}$ | |
| C$_2$H$_5$ | n-C$_6$H$_{13}$ | |
| n-C$_3$H$_7$ | CH$_3$ | C 38 S$_B$ 90 N 184.2 I; Δn = +0.119; Δε = 1.58 |
| n-C$_3$H$_7$ | C$_2$H$_5$ | |
| n-C$_3$H$_7$ | n-C$_3$H$_7$ | |
| n-C$_3$H$_7$ | n-C$_5$H$_{11}$ | |
| n-C$_3$H$_7$ | OCH$_3$ | C 71 S$_B$ 104 N 209.7 I; Δn = +0.129; Δε = 1.02 |
| n-C$_5$H$_{11}$ | CH$_3$ | |
| n-C$_5$H$_{11}$ | C$_2$H$_5$ | |
| n-C$_5$H$_{11}$ | n-C$_3$H$_7$ | |
| n-C$_5$H$_{11}$ | n-C$_5$H$_{11}$ | |
| n-C$_5$H$_{11}$ | n-C$_6$H$_{13}$ | |
| n-C$_6$H$_{13}$ | CH$_3$ | |
| n-C$_6$H$_{13}$ | C$_2$H$_5$ | |
| n-C$_6$H$_{13}$ | n-C$_3$H$_7$ | |

-continued

| $R^1$ | $R^2$ |
|---|---|
| n-C$_6$H$_{13}$ | n-C$_5$H$_{11}$ |
| n-C$_6$H$_{13}$ | n-C$_6$H$_{13}$ |

EXAMPLE 3

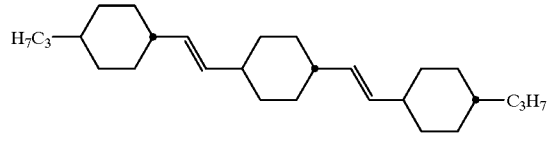

Step 3.1

Under a nitrogen atmosphere, 0.21 mol of 1,4-cyclohexanedione and 0.53 mol of methoxytriphenylphosphonium chloride are dissolved in 200 ml of THF, and 0.56 mol of potassium tert-butoxide are added at room temperature with stirring. The mixture is stirred for 2 hours, water and dilute hydrochloric acid are added, the mixture is subjected to conventional work-up.

Step 3.2

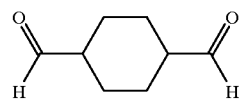

The product from step 3.1 is dissolved in 915 ml of THF, 230 ml of 2N HCl are added, and the mixture is stirred for 2 hours at the boil. The mixture is subsequently subjected to conventional work-up.

Step 3.3

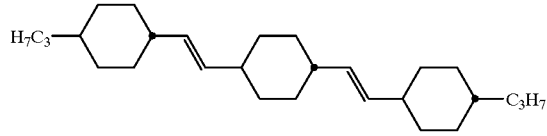

Under a nitrogen atmosphere, 0.31 mol of trans-4-n-propylcyclohexylmethyltriphenylphosphonium iodide is suspended in 520 ml of THF, and 0.31 mol of potassium tert-butoxide is added in portions. The mixture is stirred for 1 hour at 0° C., 0.13 mol of cyclohexane-1,4-dicarbaldehyde is added, and the mixture is stirred at room temperature for 1 hour. Water and dilute hydrochloric acid are added, and the mixture is subjected to conventional work-up.

The isomerization is carried out analogously to Step 1.2.
C 98 S$_B$ 190 N 235.7 I The following compounds of the formula

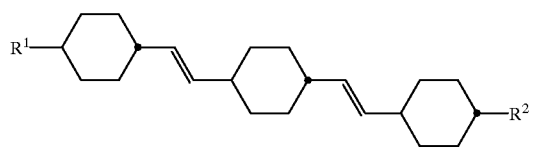

are prepared analogously:

| R¹ | R² |
|---|---|
| CH₃ | CH₃ |
| CH₃ | C₂H₅ |
| CH₃ | n-C₃H₇ |
| CH₃ | n-C₅H₁₁ |
| CH₃ | n-C₆H₁₃ |
| C₂H₅ | CH₃ |
| C₂H₅ | C₂H₅ |
| C₂H₅ | n-C₃H₇ |
| C₂H₅ | n-C₅H₁₁ |
| C₂H₅ | n-C₆H₁₃ |
| n-C₃H₇ | CH₃ |
| n-C₃H₇ | C₂H₅ |
| n-C₃H₇ | n-C₃H₇ |
| n-C₃H₇ | n-C₅H₁₁ |
| n-C₃H₇ | n-C₆H₁₃ |
| n-C₅H₁₁ | CH₃ |
| n-C₅H₁₁ | C₂H₅ |
| n-C₅H₁₁ | n-C₃H₇ |
| n-C₅H₁₁ | n-C₅H₁₁ |
| n-C₅H₁₁ | n-C₆H₁₃ |
| n-C₆H₁₃ | CH₃ |
| n-C₆H₁₃ | C₂H₅ |
| n-C₆H₁₃ | n-C₃H₇ |
| n-C₆H₁₃ | n-C₅H₁₁ |
| n-C₆H₁₃ | n-C₆H₁₃ |

EXAMPLE 4 a)

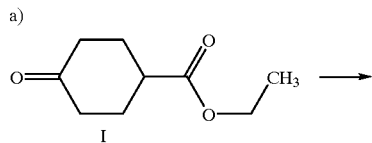

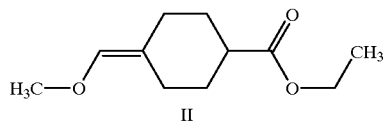

Under a nitrogen atmosphere, 2.93 ml of methoxymethyltrimethyltriphenylphosphonium chloride and 2.93 mol of ethyl 4-cyclohexanonecarboxylate are dissolved in 4 l of THF, and 2.93 mol of potassium tert-butoxide are added at room temperature with stirring. The mixture is stirred for 2 hours, water and dilute hydrochloric acid are added, and the mixture is subjected to conventional work-up.

b)

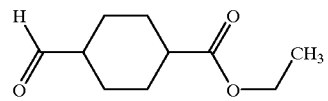

50.4 mmol of II, 1.0 g of 10% HCl, 20 ml of THF and 50.4 mmol of acetaldehyde are stirred at room temperature for 0.75 hour. Water and methyl tert-butyl ether are added, and the mixture is subjected to conventional work-up.

c)

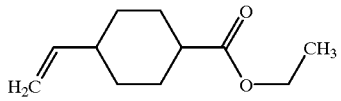

Under a nitrogen atmosphere, 46.1 mmol of potassium tert-butoxide in 20 ml of THF are added dropwise at 0° C. to 46.1 mmol of methyltriphenylphosphonium bromide dissolved in 50 ml of THF. After the mixture has been stirred for 10 minutes, 46.1 mmol of III dissolved in 20 ml of THF are added dropwise to the solution. The mixture is allowed to warm to room temperature, water and dilute HCl and methyl tert-butyl ether are added, and the mixture is subjected to conventional work-up.

d)

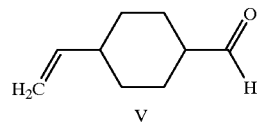

65.8 nmol of Vitride are introduced into 35 ml of toluene at 0° C., and 72.3 mmol of morpholine dissolved in 20 ml of toluene are added with stirring. The solution is added dropwise at −40° C. to 32.9 mmol of IV dissolved in 30 ml of toluene, and the mixture is stirred at from −40 to −50° for 70 minutes. Water is added at −40° C. and 10% HCl is added at −10° C. The mixture is subsequently subjected to conventional work-up.

e)

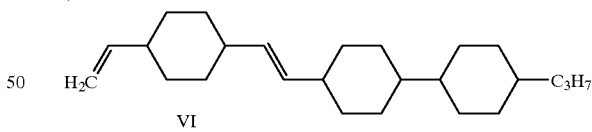

0.40 mol of potassium tert-butoxide is added in portions to 0.04 mol of V, 0.04 mol of 4[trans-4-(trans-4-propylcyclohexyl) cyclohexylmethyltriphenylphosphonium iodide and 1140 ml of THF; during this addition, the reaction temperature should not exceed 35° C. The mixture is stirred overnight at room temperature, and hydrolysed, dilute HCL is added, and the mixture is subjected to conventional work-up. C −2 $S_B$ 188 N 222.2 I; $\Delta n$=+0.888; $\Delta\epsilon$=1.03

The following compounds of the formula

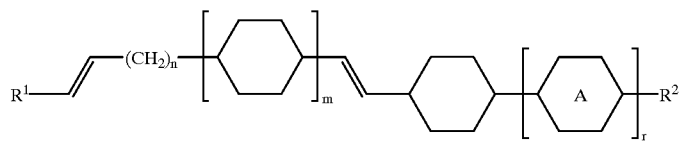

are prepared analogously:

| R¹ | n | m | r | A | R² | |
|---|---|---|---|---|---|---|
| H | 0 | 1 | 1 | -⟨H⟩- | CH₃ | C 69 S$_B$ 70 N 174.2 I; $\Delta n = +0.115$; $\Delta \epsilon = 0.82$ |
| H | 0 | 1 | 1 | -⟨H⟩- | C₂H₅ | C −9 S$_B$ 174 N 204.5 I; $\Delta n = +0.079$; $\Delta \epsilon = 0.71$ |
| H | 0 | 1 | 1 | -⟨H⟩- | n-C₅H₁₁ | |
| CH₃ | 0 | 1 | 1 | -⟨H⟩- | CH₃ | |
| CH₃ | 0 | 1 | 1 | -⟨H⟩- | C₂H₅ | C 46 S$_B$ 184 N 245.3 I; $\Delta n = +0.089$; $\Delta \epsilon = 0.96$ |
| CH₃ | 0 | 1 | 1 | -⟨H⟩- | n-C₃H₇ | C 51 S$_B$ 204 N 245.3 I; $\Delta n = +0.099$; $\Delta \epsilon = 1.55$ |
| CH₃ | 0 | 1 | 1 | -⟨H⟩- | OCH₃ | C 84 N 251.7 I; $\Delta n = +0.138$; $\Delta \epsilon = 1.12$ |
| CH₃ | 0 | 1 | 1 | -⟨H⟩- | n-C₅H₁₁ | |
| C₂H₅ | 0 | 1 | 1 | -⟨H⟩- | n-C₃H₇ | |

-continued

| | | | | A | |
|---|---|---|---|---|---|
| R¹ | n | m | r | | R² |
| $C_2H_5$ | 0 | 1 | 1 |  | $n-C_5N_{11}$ |
| H | 1 | 1 | 1 | 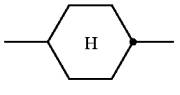 | $n-C_2H_5$ |
| H | 1 | 1 | 1 | 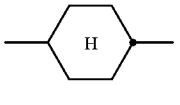 | $n-C_3H_7$ |
| H | 1 | 1 | 1 | 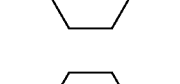 | $n-C_5H_{11}$ |
| $CH_3$ | 1 | 1 | 1 |  | $n-C_3H_7$ |
| $CH_3$ | 1 | 1 | 1 | 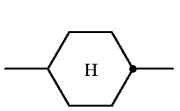 | $n-C_5H_{11}$ |
| $C_2H_5$ | 1 | 1 | 1 |  | $n-C_3H_7$ |
| $C_2H_5$ | 1 | 1 | 1 |  | $n-C_5H_{11}$ |
| H | 0 | 2 | 0 | — | $CH_3$ |
| H | 0 | 2 | 0 | — | $C_2H_5$ | C −65 $S_B$ 152 N 183.7 I; $\Delta n = +0.077$; $\Delta \epsilon = 1.01$
| H | 0 | 2 | 0 | — | $n-C_3H_7$ | C −11 $S_B$ 168 N 217.1 I; $\Delta n = +0.084$; $\Delta \epsilon = 1.03$
| H | 0 | 2 | 0 | — | $n-C_4H_9$ |
| H | 0 | 2 | 0 | — | $n-C_5H_{11}$ |
| $CH_3$ | 0 | 2 | 0 | — | $CH_3$ |
| $CH_3$ | 0 | 2 | 0 | — | $C_2H_5$ |
| $CH_3$ | 0 | 2 | 0 | — | $n-C_3H_7$ | C 22 $S_B$ 189 N 253.2 I; $\Delta n = +0.098$; $\Delta \epsilon = 2.15$
| $CH_3$ | 0 | 2 | 0 | — | $n-C_4H_9$ |
| $CH_3$ | 0 | 2 | 0 | — | $n-C_5H_{11}$ |
| $C_2H_5$ | 0 | 2 | 0 | — | $CH_3$ |
| $C_2H_5$ | 0 | 2 | 0 | — | $C_2H_5$ |
| $C_2H_5$ | 0 | 2 | 0 | — | $n-C_3H_7$ |
| $C_2H_5$ | 0 | 2 | 0 | — | $n-C_4H_9$ |
| $C_2H_5$ | 0 | 2 | 0 | — | $n-C_5H_{11}$ |
| H | 1 | 2 | 0 | — | $CH_3$ |
| H | 1 | 2 | 0 | — | $C_2H_5$ |
| H | 1 | 2 | 0 | — | $n-C_3H_7$ |

-continued

| R¹ | n | m | r | A | R² | |
|---|---|---|---|---|---|---|
| H | 1 | 2 | 0 | — | n-$C_4H_9$ | |
| H | 1 | 2 | 0 | — | n-$C_5H_{11}$ | |
| $CH_3$ | 1 | 2 | 0 | — | $CH_3$ | |
| $CH_3$ | 1 | 2 | 0 | — | $C_2H_5$ | |
| $CH_3$ | 1 | 2 | 0 | — | n-$C_3H_7$ | |
| $CH_3$ | 1 | 2 | 0 | — | n-$C_4H_9$ | |
| $CH_3$ | 1 | 2 | 0 | — | n-$C_5H_{11}$ | |
| $C_2H_5$ | 1 | 2 | 0 | — | $CH_3$ | |
| $C_2H_5$ | 1 | 2 | 0 | — | $C_2H_5$ | |
| $C_2H_5$ | 1 | 2 | 0 | — | n-$C_3H_7$ | |
| $C_2H_5$ | 1 | 2 | 0 | — | n-$C_4H_9$ | |
| $C_2H_5$ | 1 | 2 | 0 | — | n-$C_5H_{11}$ | |
| H | 0 | 1 | 1 | ⟨phenyl⟩ | $CH_3$ | C 61 $S_B$ 70 N 174 I |
| H | 0 | 1 | 1 | ⟨phenyl⟩ | $C_2H_5$ | C 56 $S_B$ 122 N 157.3 I; $\Delta n = +0.107$; $\Delta \epsilon = 0.26$ |
| H | 0 | 1 | 1 | ⟨phenyl⟩ | $OCH_3$ | C 63 $S_B$ 92 N 204.5 I; $\Delta n = +0.126$; $\Delta \epsilon = 1.12$ |
| H | 0 | 1 | 1 | ⟨phenyl⟩ | n-$C_3H_7$ | C 30 $S_B$ 133 N 168 I; $\Delta n = +0.108$; $\Delta \epsilon = 0.58$ |
| H | 0 | 1 | 1 | ⟨phenyl⟩ | $OC_2H_5$ | C 51 $S_B$ 100 N 208.8 I; $\Delta n = +0.095$ |
| H | 0 | 1 | 1 | ⟨phenyl⟩ | $OCH_2CF_3$ | |
| H | 0 | 1 | 1 | ⟨phenyl⟩ | $OCHF_2$ | |
| $H_3C$ | 0 | 1 | 1 | ⟨phenyl⟩ | $CH_3$ | C 78 N 255.7 I; $\Delta n = +0.132$; $\Delta \epsilon = 1.01$ |
| $H_3C$ | 0 | 1 | 1 | ⟨phenyl⟩ | $C_2H_5$ | C 71 $S_B$ 113 N 212.6 I; $\Delta n = +0.125$; $\Delta \epsilon = 0.7$ |
| $H_3C$ | 0 | 1 | 1 | ⟨phenyl⟩ | n-$C_3H_7$ | C 36 $S_B$ 142 N 214.8 I; $\Delta n = +0.128$; $\Delta \epsilon = 1.45$ |

-continued

| R¹ | n | m | r | A | R² | |
|---|---|---|---|---|---|---|
| H₃C | 0 | 1 | 1 | (phenyl) | OCH₃ | C 85 S_B (83) N 253 I |
| H₃C | 0 | 1 | 1 | (phenyl) | OC₂H₅ | C 77 S_B 97 N 256.1 I; $\Delta n = +0.143$; $\Delta \epsilon = 1.91$ |
| H₃C | 0 | 1 | 1 | (phenyl) | OCF₃ | |
| H₃C | 0 | 1 | 1 | (phenyl) | OCH₂CF₃ | |
| H₃C | 0 | 1 | 1 | (phenyl) | OCHF₂ | |
| H₅C₂ | 0 | 1 | 1 | (phenyl) | CH₃ | C 62 S_B 108 N 214.7 I; $\Delta n = +0.125$; $\Delta \epsilon = 0.8$ |
| H₅C₂ | 0 | 1 | 1 | (phenyl) | C₂H₅ | |
| H₅C₂ | 0 | 1 | 1 | (phenyl) | n-C₃H₇ | |
| H | 0 | 1 | 1 | (fluorophenyl) | CH₃ | |
| H | 0 | 1 | 1 | (fluorophenyl) | C₂H₅ | |
| H | 0 | 1 | 1 | (fluorophenyl) | OCH₃ | |

-continued
| R¹ | n | m | r | | R² |
|---|---|---|---|---|---|
| H | 0 | 1 | 1 | 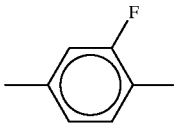 | OC₂H₅ |
| H | 0 | 1 | 1 | 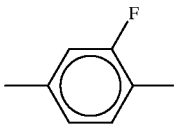 | CN |
| H | 0 | 1 | 1 | 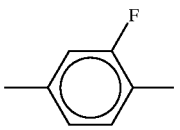 | OCF₃ |
| H | 0 | 1 | 1 | 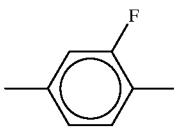 | OCH₂CF₃ |
| H | 0 | 1 | 1 | 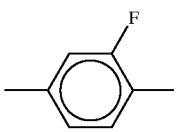 | OCHF₂ |
| H₃C | 0 | 1 | 1 | 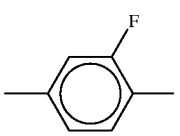 | CH₃ |
| H₃C | 0 | 1 | 1 | 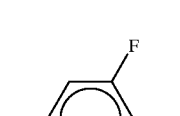 | C₂H₅ |
| H₃C | 0 | 1 | 1 | 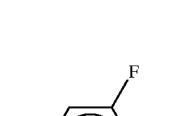 | OCH₃ |
| H₃C | 0 | 1 | 1 | 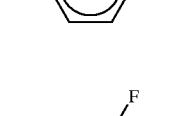 | OC₂H₅ |

-continued
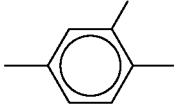
| R¹ | n | m | r | | R² |
|---|---|---|---|---|---|
| H₃C | 0 | 1 | 1 | 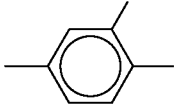 | OCH₂CF₃ |
| H₃C | 0 | 1 | 1 | 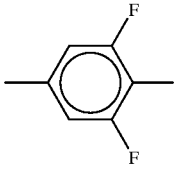 | OCHF₂ |
| H | 0 | 1 | 1 | 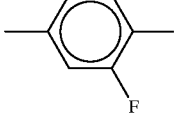 | CH₃ |
| H | 0 | 1 | 1 | 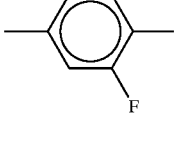 | C₂H₅ |
| H | 0 | 1 | 1 | 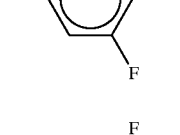 | OCH₃ |
| H | 0 | 1 | 1 | 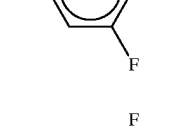 | OC₂H₅ |
| H | 0 | 1 | 1 | 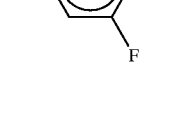 | OCH₂CF₃ |
| H | 0 | 1 | 1 |  | OCHF₂ |

-continued

| R¹ | n | m | r | | R² | |
|---|---|---|---|---|---|---|
| H₃C | 0 | 1 | 1 | 2,3-difluorophenyl | CH₃ | |
| H₃C | 0 | 1 | 1 | 2,3-difluorophenyl | C₂H₅ | |
| H₃C | 0 | 1 | 1 | 2,3-difluorophenyl | OCH₃ | |
| H₃C | 0 | 1 | 1 | 2,3-difluorophenyl | OC₂H₅ | |
| H₃C | 0 | 1 | 1 | 2,3-difluorophenyl | OCH₂CF₃ | |
| H₃C | 0 | 1 | 1 | 2,3-difluorophenyl | OCHF₂ | |
| H | 0 | 1 | 0 | — | CH₃ | |
| H | 0 | 1 | 0 | — | C₂H₅ | |
| H | 0 | 1 | 0 | — | n-C₃H₇ | C 28 N 43.8 I; $\Delta n = +0.052$; $\Delta \epsilon = -1.35$ |
| H | 0 | 1 | 0 | — | n-C₄H₉ | C 7 S$_B$ 40 N 45.9 I; $\Delta n = +0.045$, $\Delta \epsilon = -1$ |
| H | 0 | 1 | 0 | — | n-C₅H₁₁ | C 0 S$_B$ 39 N 47.9 I; $\Delta n = +0.045$, $\Delta \epsilon = -1.1$ |
| CH₃ | 0 | 1 | 0 | — | CH₃ | |

-continued
| R¹ | n | m | r | | R² | |
|---|---|---|---|---|---|---|
| CH₃ | 0 | 1 | 0 | — | C₂H₅ | C 33 S_B (20) N 45.5 I; $\Delta n = +0.057$; $\Delta\epsilon = -1.22$ |
| CH₃ | 0 | 1 | 0 | — | n-C₃H₇ | C 56 N 89.6 I; $\Delta n = +0.069$; $\Delta\epsilon = -0.64$ |
| CH₃ | 0 | 1 | 0 | — | n-C₄H₉ | C 30 S_B 62 N 89 I; $\Delta n = +0.067$; $\Delta\epsilon = -0.74$ |
| CH₃ | 0 | 1 | 0 | — | n-C₅H₁₁ | C 18 S_B 70 N 100.0 I |
| C₂H₅ | 0 | 1 | 0 | — | n-C₃H₇ | C 27 S_B 75 N 81.1 I; $\Delta n = +0.064$; $\Delta\epsilon = -1.1$ |
| C₂H₅ | 0 | 1 | 0 | 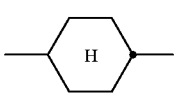 | C₂H₅ | |
| C₂H₅ | 0 | 1 | 0 |  | n-C₃H₇ | |
| C₂H₅ | 0 | 1 | 0 |  | n-C₅H₁₁ | |
| H | 1 | 1 | 0 |  | CH₃ | |
| H | 1 | 1 | 0 | 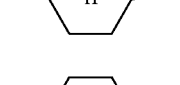 | C₂H₅ | |
| H | 1 | 1 | 0 | 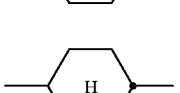 | n-C₃H₇ | |
| H | 1 | 1 | 0 |  | n-C₅H₁₁ | |
| CH₃ | 1 | 1 | 0 |  | CH₃ | |
| CH₃ | 1 | 1 | 0 |  | C₂H₅ | |
| CH₃ | 1 | 1 | 0 |  | n-C₃H₇ | |

-continued

[Structure: R¹—(ring A)ₙ—(linking)ᵣ—R²]

| R¹ | n | m | r | (ring) | R² | |
|---|---|---|---|---|---|---|
| $CH_3$ | 1 | 1 | 0 | (H-cyclohexyl) | $n\text{-}C_5H_{11}$ | |
| $C_2H_5$ | 1 | 1 | 0 | (H-cyclohexyl) | $CH_3$ | |
| $C_2H_5$ | 1 | 1 | 0 | (H-cyclohexyl) | $C_2H_5$ | |
| $C_2H_5$ | 1 | 1 | 0 | (H-cyclohexyl) | $n\text{-}C_3H_7$ | |
| $C_2H_5$ | 1 | 1 | 0 | (H-cyclohexyl) | $n\text{-}C_5H_{11}$ | |
| H | 0 | 1 | 0 | — | $CH=CH_2$ | |
| H | 0 | 1 | 0 | — | $CH=CH\text{—}CH_3$ | C 52 N 63.1 I; $\Delta n = +0.069$; $\Delta\epsilon = -0.85$ |
| $CH_3$ | 0 | 1 | 0 | — | $CH=CH_2$ | C 51 N 61.1 I; |
| $CH_3$ | 0 | 1 | 0 | — | $CH=CH\text{—}CH_3$ | C 86 N 121.3 I; $\Delta n = +0.095$ |
| $CH_3$ | 0 | 1 | 0 | — | $CH=CH\text{—}C_2H_5$ | C 60 $S_B$ 61 N 112 I |
| $C_2H_5$ | 0 | 1 | 0 | — | $CH=CH_2$ | |
| $C_2H_5$ | 0 | 1 | 0 | — | $CH=CH\text{—}CH_3$ | C 60 $S_B$ 61 N 112.4 I; $\Delta n = +0.086$; $\Delta\epsilon = -0.4$ |
| $n\text{-}C_3H_7$ | 0 | 1 | 0 | — | $CH=CH_2$ | |
| $n\text{-}C_3H_7$ | 0 | 1 | 0 | — | $CH=CH\text{—}CH_3$ | |
| $n\text{-}C_4H_9$ | 0 | 1 | 0 | — | $CH=CH_2$ | |
| $n\text{-}C_4H_9$ | 0 | 1 | 0 | — | $CH=CH\text{—}CH_3$ | |
| $n\text{-}C_5H_{11}$ | 0 | 1 | 0 | — | $CH=CH_2$ | |
| $n\text{-}C_5H_{11}$ | 0 | 1 | 0 | — | $CH=CH\text{—}CH_3$ | |
| H | 0 | 1 | 0 | — | $CH=CH\text{—}C_2H_5$ | |
| H | 0 | 1 | 0 | — | $CH=CH\text{—}C_3H_7$ | |
| $H_3C$ | 0 | 1 | 0 | — | $CH=CH\text{—}C_2H_5$ | |
| $H_3C$ | 0 | 1 | 0 | — | $CH=CH\text{—}C_3H_7$ | |
| H | 0 | 1 | 1 | (H-cyclohexyl) | $CH=CH_2$ | |
| H | 0 | 1 | 1 | (H-cyclohexyl) | $CH=CH\text{—}CH_3$ | |
| $CH_3$ | 0 | 1 | 1 | (H-cyclohexyl) | $CH=CH_2$ | |

-continued

| $R^1$ | n | m | r | A | $R^2$ |
|---|---|---|---|---|---|
| $CH_3$ | 0 | 1 | 1 | H | $CH=CH-CH_3$ |
| n-$C_5H_{11}$ | 0 | 1 | 1 | H | $CH=CH_2$ |
| n-$C_5H_{11}$ | 0 | 1 | 1 | H | $CH=CH-CH_3$ |
| H | 0 | 1 | 1 | H | $CH=CH-C_2H_5$ |
| H | 0 | 1 | 1 | H | $CH=CH-C_3H_7$ |
| $H_3C$ | 0 | 1 | 1 | H | $CH=CH-C_2H_5$ |
| $H_3C$ | 0 | 1 | 1 | H | $CH=CH-C_3H_7$ |
| H | 0 | 1 | 1 | (phenyl) | $CH_2CHCH=CH_2$ |
| $H_3C$ | 0 | 1 | 1 | (phenyl) | $CH_2CH_2CH=CH_2$  C 42 $S_B$ 142 N 220.3 I; $\Delta n = +0.136$; $\Delta\epsilon = 1.0$ |

Mixture Examples

Example M1

| PCH-3 | 21.0% | Clearing point [° C.]: | +86 |
|---|---|---|---|
| PCH-5 | 15.0% | $\Delta n$ [589 nm; 20° C]: | +0.1428 |
| PCH-302 | 23.0% | STN 240° | |
| K6 | 5.0% | d · $\Delta n$ [μm]: | 0.85 |
| BCH-32 | 7.0% | $V_{(10,0,20)}$ [V]: | 2.38 |
| ECCP-31 | 5.0% | $V_{90}/V_{10}$: | 1.0305 |
| ECCP-32 | 5.0% | $t_{ave}$ [ms]: | 263 |
| CPTP-301 | 5.0% | | |
| CPTP-302 | 4.0% | | |

-continued

| CPTP-303 | 4.0% |
|---|---|
| CVCP-3-1 | 6.0% |

Example M2

| PCH-3 | 21.0% | Clearing point [° C.]: | +86 |
|---|---|---|---|
| PCH-5 | 15.0% | $\Delta n$ [589 nm; 20° C]: | +0.1416 |
| PCH-302 | 24.0% | STN 240° | |
| K6 | 6.0% | d · $\Delta n$ [μm]: | 0.85 |

| | |
|---|---|
| BCH-32 | 8.0% |
| ECCP-31 | 4.0% |
| ECCP-32 | 4.0% |
| CPTP-301 | 4.0% |
| CPTP-302 | 4.0% |
| CPTP-303 | 4.0% |
| CVCP-3-3 | 6.0% |
| $V_{(10,0,20)}$ [V]: | 2.34 |
| $V_{90}/V_{10}$: | 1.036 |
| $t_{ave}$ [ms]: | 248 |

Example M3

An STN display having the following parameters:

| | |
|---|---|
| Twist | 240° |
| MuX | 1:240 |
| d · Δn [μm] | 0.85 | contains a nematic mixture having the following properties:

| | |
|---|---|
| Clearing point: | 90.1° C. |
| Δn [589 nm; 20° C.]: | 0.1421 |
| d/p | 0.53 | and consisting of:

| | |
|---|---|
| ME2N.F | 2.0% |
| ME3N.F | 3.0% |
| PCH-3 | 20.0% |
| PCH-5 | 6.0% |
| PTP-201 | 5.0% |
| BCH-32 | 8.0% |
| BCH-52 | 8.0% |
| CPTP-301 | 5.0% |
| CPTP-302 | 5.0% |
| CPTP-303 | 4.0% |
| PCH-302 | 6.0% |
| CCH-34 | 5.0% |
| CCH-35 | 5.0% |
| CVC-V1-2 | 6.0% |
| CVC-V1-3 | 6.0% |
| CVC-V1-4 | 6.0% | has the following switching behavior:

| | |
|---|---|
| $V_{10}$ | 2.39 V |
| $V_{90}/V_{10}$ | 1.051 |
| $t_{ave}$ | 217 ms |

Example M4

An STN display as described in M3 contains a nematic mixture having the following properties:

| | |
|---|---|
| Clearing point: | 93.1° C. |
| Δn [589 nm; 20° C.]: | 0.1408 |
| d/p | 0.53 | and consists of:

| | |
|---|---|
| ME-2N.F | 2.0% |
| K6 | 6.0% |
| K9 | 6.0% |
| PCH-3 | 18.0% |
| BCH-32 | 7.0% |
| BCH-52 | 7.0% |
| CPTP-301 | 5.0% |
| CPTP-302 | 4.0% |
| CPTP-303 | 4.0% |
| CCH-34 | 5.0% |
| CCH-35 | 4.0% |
| CVC-V1-2 | 10.0% |
| CVC-V1-3 | 10.0% |
| CVC-V1-4 | 10.0% |
| CBC-33 | 2.0% | has the following switching behavior:

| | |
|---|---|
| $V_{10}$ | 2.496 V |
| $V_{90}/V_{10}$ | 1.048 |
| $t_{ave}$ | 213 ms |

Example M5

An STN display as described in M3 contains a nematic mixture having the following properties:

Clearing point: 87.6° C.

Δn [589 nm; 20° C.]: 0.1397 d/p: 0.52 and consists of:

| | |
|---|---|
| ME-2N.F | 2.0% |
| K6 | 4.0% |
| K9 | 5.9% |
| PCH-3 | 22.0% |
| PTP-201 | 2.0% |
| BCH-32 | 5.0% |
| BCH-52 | 5.0% |
| CPTP-301 | 5.0% |
| CPTP-302 | 5.0% |
| CPTP-303 | 5.0% |
| CCH-34 | 5.0% |
| CCH-35 | 5.0% |
| CVC-V1-2 | 10.0% |
| CVC-V1-3 | 10.0% |
| CVC-V1-4 | 10.0% | has the following switching behavior:

| | |
|---|---|
| $V_{10}$ | 2.44 V |
| $V_{90}/V_{10}$ | 1.039 |
| $t_{ave}$ | 223 ms |

Example M6

An STN display as described in M3 contains a nematic mixture having the following properties:

Clearing point: 86.4° C.

Δn [589 nm; 20° C.]: 0.1395 d/p: 0.52 and consists of:

| | |
|---|---|
| ME-2N.F | 2.0% |
| K6 | 4.0% |
| K9 | 5.0% |
| PCH-3 | 22.0% |
| PTP-201 | 2.0% |
| BCH-32 | 5.0% |
| BCH-52 | 5.0% |

-continued

| | |
|---|---|
| CPTP-301 | 5.0% |
| CPTP-302 | 5.0% |
| CPTP-303 | 5.0% |
| CCH-34 | 5.0% |
| CCH-35 | 5.0% |
| CVC-V1-2 | 10.0% |
| CVC-V1-3 | 10.0% |
| CVC-V-3 | 10.0% | has the following switching behavior:

| | |
|---|---|
| $V_{10}$ | 2.432 V |
| $V_{90}/V_{10}$ | 1.042 |
| $t_{ave}$ | 215 ms |

Example M7

An STN display as described in M3 contains a nematic mixture having the following properties:

Clearing point: 85.9° C.
Δn [589 nm; 20° C.]: 0.1395
d/p: 0.52
and consists of:

| | |
|---|---|
| ME-2N.F | 2.0% |
| K6 | 4.0% |
| K9 | 5.0% |
| PCH-3 | 22.0% |
| PTP-201 | 2.0% |
| BCH-32 | 5.0% |
| BCH-52 | 5.0% |
| CPTP-301 | 5.0% |
| CPTP-302 | 5.0% |
| CPTP-303 | 5.0% |
| CCH-34 | 5.0% |
| CCH-35 | 5.0% |
| CVC-V1-2 | 10.0% |
| CVC-V1-3 | 10.0% |
| CVC-1V-V | 10.0% | has the following switching behavior:

| | |
|---|---|
| $V_{10}$ | 2.4 V |
| $V_{90}/V_{10}$ | 1.039 |
| $t_{ave}$ | 209 ms |

Examples M8–M13

The compositions of the liquid-crystalline media and the properties of the STN displays produced using them (Twist= 240°) are shown in the tables below:

TABLE I

| Example/component | M8 (%) | M9 (%) | M10 (%) | M11 (%) | M12 (%) | M13 (%) |
|---|---|---|---|---|---|---|
| K6 | 10 | 10 | 10 | 9 | 10.00 | 10 |
| K9 | 10 | 10 | 10 | 9 | 10.00 | 10 |
| K12 | 4 | 4 | 5 | — | 4.63 | — |
| ME2N.F | 4 | 2 | 2 | 2 | 2.00 | — |
| ME3N.F | — | — | — | 3 | — | 4 |
| PCH-3 | 6 | 8 | 6 | 9 | 6.74 | 8 |
| PTP-201 | 7 | 6 | 4 | 7 | 4.74 | 4 |
| BCH-32 | — | 4 | 11 | 6 | 8.41 | 5 |
| CPTP-302 | — | — | — | 2 | — | — |

TABLE I-continued

| Example/component | M8 (%) | M9 (%) | M10 (%) | M11 (%) | M12 (%) | M13 (%) |
|---|---|---|---|---|---|---|
| CPTP-303 | — | — | — | — | — | 4 |
| CCH-34 | 9 | 11 | 14 | 14 | 12.89 | 14 |
| CCH-35 | — | — | 4 | 4 | 2.52 | — |
| CVC-V1-2 | — | — | — | — | — | 6 |
| CVC-V1-3 | 20 | 15 | 15 | 15 | 15.00 | 7 |
| CVC-VI-4 | — | — | — | — | — | 6 |
| CVCP-1V-1 | 13 | 13 | 8 | — | 9.85 | 7 |
| CVCP-1V-2 | — | — | — | — | — | 7 |
| CVCP-1V-3 | — | — | — | — | — | 8 |
| CVCP-V-1 | 17 | 17 | 11 | 8 | 13.22 | — |
| CVCP-V-1 | — | — | — | 12 | — | — |

TABLE II

| Example/properties | M8 | M9 | M10 | M11 | M12 | M13 |
|---|---|---|---|---|---|---|
| Δn (589 nm) | 0.1321 | 0.1436 | 0.1387 | 0.1386 | 0.1405 | 0.1400 |
| Clearing point (° C.) | 82.2 | 86.4 | 81.7 | 82.4 | 83.5 | 87.4 |
| Pitch [μm] | −11.2 | −11.3 | −11.3 | −11.4 | −11.6 | −11.8 |
| d [μm] | 5.89 | 5.92 | 6.13 | 6.14 | 6.07 | 6.07 |
| $V_{10}$ [V] | 2.20 | 2.26 | 2.21 | 2.18 | 2.28 | 2.29 |
| $V_0/V_{10}$ | 1.020 | 1.024 | 1.050 | 1.046 | 1.041 | 1.038 |
| $t_{ave}$ [ms] | 218 | 215 | 183 | 210 | 192 | 215 |

Examples M14–M7

The compositions of the liquid-crystalline media and the properties of the STN displays produced using them (Twist= 240°) are shown in the tables below:

TABLE III

| Example/component | M14 (%) | M15 (%) | M16 (%) | M17 (%) |
|---|---|---|---|---|
| PCH-2 | 18.0 | 8.0 | 8.0 | 8.0 |
| PCH-3 | 25.0 | 25.0 | 24.0 | 24.0 |
| ME-2N.F | 3.0 | 3.0 | 2.0 | 2.0 |
| ME-3N.F | — | 3.0 | 3.0 | 3.0 |
| ME-5N.F. | — | 3.0 | 7.0 | 7.0 |
| CCH-34 | — | 6.0 | — | — |
| CVC-V1-2 | 6.0 | 6.0 | — | — |
| CVC-V1-3 | 7.0 | 10.0 | 12.0 | 12.0 |
| CVC-V1-4 | 6.0 | 9.0 | 12.0 | 12.0 |
| CVCP-1V-1 | — | 6.0 | 5.0 | 5.0 |
| CVCP-1V-2 | — | 5.0 | 6.0 | 6.0 |
| PTP-102 | 5.0 | 5.0 | 4.0 | 4.0 |
| PTP-201 | 3.0 | 6.0 | 4.0 | 4.0 |
| CPTP-301 | 3.0 | — | 4.0 | 3.0 |
| CPTP-302 | 4.0 | 5.0 | 3.0 | 3.0 |
| CPTP-303 | 3.0 | — | — | — |
| BCH-32 | 6.0 | 6.0 | 6.0 | 7.0 |
| CP-33F | 6.0 | — | — | — |
| CP-35F | 5.0 | — | — | — |

TABLE IV

| Example/properties | M14 | M15 | M16 | M17 |
|---|---|---|---|---|
| Δn (589 nm) | 0.1394 | 0.1390 | 0.1413 | 0.1397 |
| Clearing point (° C.) | 75 | 74 | 77 | 77 |
| Pitch [μm] | −11.3 | −11.4 | −11.4 | −11.3 |
| d [μm] | 6.11 | 6.12 | 6.02 | 6.08 |
| $V_{10}$ [V] | 1.86 | 1.87 | 1.78 | 1.78 |

TABLE IV-continued

| Example/properties | M14 | M15 | M16 | M17 |
|---|---|---|---|---|
| $V_{90}/V_{10}$ | 1.031 | 1.036 | 1.030 | 1.037 |
| $t_{ave}$ [ms] | 280 | 228 | 249 | 240 |

TABLE V-continued

| Example/component | M18 (%) | M19 (%) | M20 (%) | M21 (%) | M22 (%) | M23 (%) | M24 (%) | M25 (%) |
|---|---|---|---|---|---|---|---|---|
| CVC-V-3 | 10 | 10 | — | 8 | 6 | — | — | — |
| CVC-V-4 | — | — | — | 5 | 4 | — | — | — |

TABLE VI

| Example/properties | M18 | M19 | M20 | M21 | M22 | M23 | M24 | M25 |
|---|---|---|---|---|---|---|---|---|
| Δn | 0.1409 | 0.1403 | 0.1390 | 0.1390 | 0.1398 | 0.1408 | 0.1262 | 0.1271 |
| Clearing point (° C.) | 87.8 | 83.3 | 83.2 | 84.8 | 83.3 | 82.6 | 111 | 108 |
| S→N | <−15 | <−15 | <−15 | <−15 | <−15 | <−15 | <0 | <−30 |
| Pitch [μm] | −10.91 | −10.99 | −11.55 | −11.55 | −11.20 | −11.40 | — | — |
| HTP [1/μm] | −10.32 | −10.72 | −9.70 | −10.05 | 10.44 | −10.36 | — | — |
| d [μm] | 6.03 | 6.06 | 6.12 | 6.12 | 6.07 | 6.04 | — | — |
| d · dn | 0.85 | 0.85 | 0.85 | 0.85 | 0.85 | 0.85 | 0.85 | 0.85 |
| d/p | 0.55 | 0.55 | 0.53 | 0.53 | 0.54 | 0.53 | — | — |
| $V_{10}$ | 2.283 | 2.183 | 2.256 | 2.285 | 2.272 | 2.131 | 2.26 | 2.21 |
| $V_{90}$ | 2.382 | 2.248 | 2.374 | 2.392 | 2.373 | 2.222 | — | — |
| $V_{90}/V_{10}$ | 1.043 | 1.030 | 1.052 | 1.047 | 1.044 | 1.043 | 1.034 | 1.036 |
| t-ave [m] | 193 | 215 | 179 | 204 | 203 | 185 | 258 | 275 |

Examples M18–25

The compositions of the liquid-crystalline media and the properties of the STN displays produced using them (Twist= 240°) are shown in the tables below:

TABLE V

| Example/component | M18 (%) | M19 (%) | M20 (%) | M21 (%) | M22 (%) | M23 (%) | M24 (%) | M25 (%) |
|---|---|---|---|---|---|---|---|---|
| ME2N.F | 2 | 2 | 2 | 2 | 2 | 2 | 2.5 | 2.5 |
| ME3N.F | 2 | 2 | 2 | — | — | 3 | 3.5 | 3.5 |
| ME4N.F | — | — | — | — | — | — | 6.0 | 6.0 |
| K6 | 6 | 6 | 6 | 6 | 6 | 6 | — | — |
| K9 | 4 | 4 | 4 | 5 | 6 | 5 | 10.0 | 10.0 |
| PCH-3 | 20 | 20 | 20 | 18 | 18 | 17 | 10.0 | 10.0 |
| ECCP-3F | — | — | — | — | — | — | 13.0 | — |
| CCP-2OCF$_3$ | — | — | — | — | — | — | 6.0 | 6.0 |
| CCP-3OCF$_3$ | — | — | — | — | 6 | 6 | 6.0 | 6.0 |
| CCP-4OCF$_3$ | — | — | — | — | — | — | 6.0 | 6.0 |
| CCP-5OCF$_3$ | — | — | — | — | — | — | 4.0 | 6.0 |
| PTP-20F | — | — | — | — | — | — | — | — |
| PTP-102 | 4 | 3 | 4 | 4 | 3 | 3 | 4.0 | — |
| PTP-201 | 3 | 3 | 4 | 4 | 4 | 4 | 4.0 | — |
| BCH-32 | 9 | 8 | 10 | 7 | 11 | 9 | — | — |
| BCH-52 | — | — | — | 7 | — | — | — | — |
| CPTP-301 | 4 | 4 | 4 | 3 | 2 | 4 | — | 5.0 |
| CPTP-302 | — | — | — | — | — | — | — | 5.0 |
| PCH-301 | — | 8 | — | — | — | 6 | — | — |
| PCH-302 | — | — | — | — | 9 | — | — | 15.0 |
| CCH-34 | 7 | 6 | 7 | 8 | 7 | 8 | — | — |
| CCH-35 | 6 | — | 7 | 7 | — | — | — | — |
| CCH-301 | — | — | — | — | — | — | — | 2.0 |
| CBC-33 | 3 | 4 | — | — | — | — | — | — |
| CCH-3-2V | — | — | 15 | — | — | 15 | — | — |
| CVCP-1V-1 | 6 | 6 | 6 | 4 | 5 | 6 | 12.0 | 8.0 |
| CVCP-V-1 | 9 | 9 | 9 | 7 | 7 | 8 | 12.0 | 8.0 |
| CVCP-1V-1 | — | — | — | — | — | 4 | — | — |
| CVCP-1V-2 | — | — | — | — | — | — | 5.0 | — |
| CVCP-V-1 | — | — | — | 5 | 6 | — | — | — |
| CVC-V1-3 | 5 | 5 | — | — | — | — | 11.0 | 6.0 |

Example M26

A liquid-crystalline medium is prepared which consists of:

| | | | |
|---|---|---|---|
| ME2N.F | 2.0% | Δn [589 nm, 20° C.] | 0.1390 |
| K6 | 6.0% | Clearing point | 84.6° C. |
| K9 | 5.0% | $V_{10}$ | 2.265 V |
| PCH-3 | 18.0% | $V_{90}/V_{10}$ | 1.045 |
| PTP-102 | 4.0% | $t_{ave}$ [ms] | 200 |
| PTP-201 | 4.0% | | |
| BCH-32 | 7.0% | | |
| BCH-52 | 7.0% | | |
| CPTP-301 | 3.0% | | |
| CCH-34 | 8.0% | | |
| CCH-35 | 7.0% | | |
| CVCP-1V-1 | 4.0% | | |
| CVCP-V-1 | 7.0% | | |
| CVCP-V-1 | 5.0% | | |
| CVC-V-3 | 8.0% | | |
| CVC-V-4 | 5.0% | | |

Comparative Example 1

An STN display as described in Example M3:

| | | | |
|---|---|---|---|
| PCH-3 | 21.0% | Clearing point [° C.] | +85 |
| PCH-5 | 15.0% | Δn [589 nm] | +0.1413 |
| PCH-302 | 23.0% | STN 240° | |
| K6 | 4.0% | d.Δn [μm] | 0.85 |
| BCH-32 | 7.0% | d/p | 0.54 |
| CCP-2OCF$_3$ | 4.0% | $VC_{10.0.20}$ [V] | 2.36 |
| CCP-3OCF$_3$ | 2.0% | $V_{90}/V_{10}$ | 1.042 |
| ECCP-31 | 5.0% | $t_{ave}$ [ms] | 245 |
| ECCP-32 | 5.0% | | |
| CPTP-301 | 5.0% | | |

-continued

| | |
|---|---|
| CPTP-302 | 5.0% |
| CPTP-303 | 4.0% |

Comparative Example 2

An STN display as described in Example 20:

| | | | |
|---|---|---|---|
| ME2N.F | 4.0% | Clearing point [° C.] | +87.2 |
| ME3N.F | 3.0% | Δn [589 nm] | 0.1365 |
| PTP-20F | 4.0% | STN 240° | |
| BCH-32 | 6.0% | d.Δn [μm] | 0.85 |
| CCH-34 | 3.0% | $V_{10}$ [V] | 2.26 |
| CCH-3-2V | 29.0% | $V_{90}/V_{10}$ | 1.038 |
| PCH-1V-N | 25.0% | $t_{ave}$ [ms] | 208 ns |
| PCH-3V-N | 5.0% | | |
| BCH-3V-2 | 21.0% | | |

Example M27

| | | | |
|---|---|---|---|
| PCH-2 | 10.0% | Clearing point [° C.]: | 89 |
| PCH-3 | 24.0% | Δn [589 nm, 20° C.]: | +0.1395 |
| ME2N.F | 2.0% | Δε [1 kHz, 20° C.]: | 7.5 |
| CVC-3V | 5.0% | d · Δn [μm]: | 0.85 |
| CVC-3-V1 | 4.0% | d/p: | 0.53 |
| CVCP-V-1 | 6.0% | $V_{(10,0,20)}$ | 2.20 |
| CVCP-1V-1 | 6.0% | $V_{90}/V_{10}$ [V]: | 3.4% |
| CVCP-V-1 | 7.0% | | |
| PTP-102 | 4.0% | | |
| PTP-201 | 5.0% | | |
| CPTP-301 | 5.0% | | |
| BCH-32 | 8.0% | | |
| BCH-52 | 5.0% | | |
| CCH-34 | 9.0% | | |

We claim:

1. Supertwist liquid-crystal display containing
   two plane-parallel outer plates which, together with a frame, form a cell,
   a nematic liquid-crystal mixture of positive dielectric anisotropy which is present in the cell,
   electrode layers with superposed alignment layers on the inside of the outer plates,
   a tilt angle between the longitudinal axis of the molecules at the surface of the outer plates and the outer plates of from about 1 degree to 30 degrees, and
   a twist angle of the liquid-crystal mixture in the cell from alignment layer to alignment layer with a value of between 100 and 600°,
   a nematic liquid-crystal mixture consisting of
   a) 20–90% by weight of a liquid-crystalline component A consisting of one or more compounds having a dielectric anisotropy of greater than +1.5;
   b) 10–65% by weight of a liquid-crystalline component B consisting of one or more compounds having a dielectric anisotropy of between −1.5 and +1.5;
   c) 0–20% by weight of a liquid-crystalline component D consisting of one or more compounds having a dielectric anisotropy of below −1.5, and
   d) an optically active component C in an amount such that the ratio between the layer thickness (separation of the plane-parallel outer plates) and the natural pitch of the chiral nematic liquid-crystal mixture is from about 0.2 to 1.3, wherein
   component B comprises at least one compound of the formula I

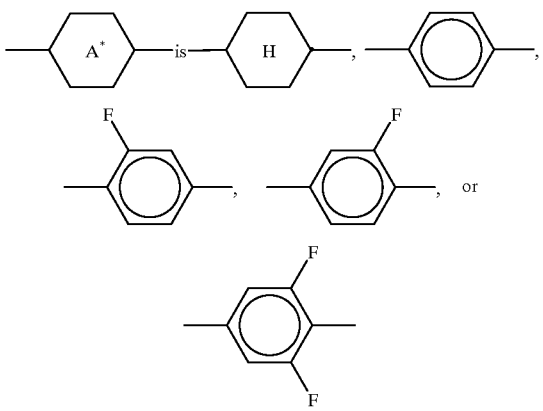

in which $R^1$ is an alkyl, alkoxy or alkenyl radical having 1 to 10 carbon atoms which is unsubstituted or monosubstituted by CN or $CF_3$ or at least monosubstituted by halogen, optionally one or more $CH_2$ groups in this radical being replaced by —O—, $R^2$ is $(CH_2)_n$—CH=CH—$R^a$ or $(CH_2)_n$—CH=$CH_2$, and, in the case where R=1, $R^2$ is alternatively $R^a$, $R^a$ is a straight-chain alkyl having 1–6 carbon atoms, n is 0–6, p is 0 or 1, r is 0, or 1 and s is 1 or 2.

2. A display according to claim 1, wherein component A comprises compounds of the formulae II and III in which
R is an alkyl group having 1 to 12 carbon atoms, one or two non-adjacent $CH_2$ groups optionally being replaced by —O—, —CH=CH—, —CO—, —OCO— or —COO—,

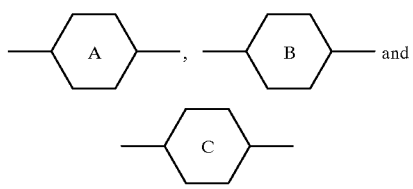

are each, independently of one another,

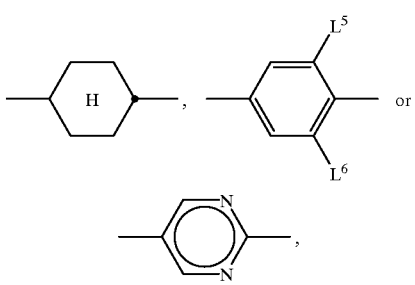

$L^{1-6}$ are each, independently of one another, H or F,
$Z^1$ is —COO—, —CH$_2$CH$_2$— or a single bond,
$Z^2$ is —CH$_2$CH$_2$—, —COO—, —C≡C— or a single bond,
Q is —CF$_2$—, —CHF—, —OCF$_2$—, —OCFH— or a single bond,
Y is F or Cl,
a is 1 or 2, and
b is 0 or 1.

3. A display according to claim 1, wherein component A comprises at least one compound of the formulae IIa to IId

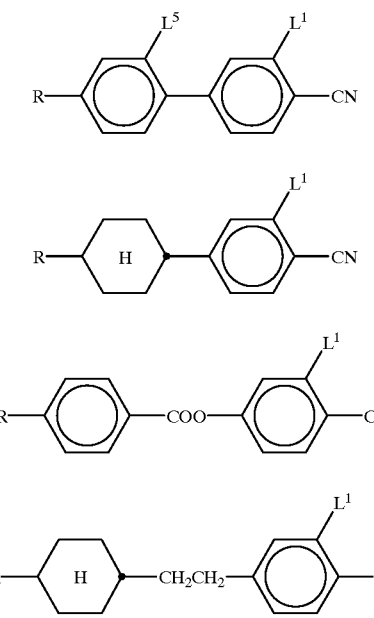

in which
  R is an alkyl group having 1 to 12 carbon atoms, one or two non-adjacent CH$_2$ groups optionally being replaced by —O—, —CH=CH—, —CO—, —OCO— or —COO—,
and $L^1$ and $L^5$ are independently H or F.

4. A display according to claim 1, wherein component B comprises one or more compounds of the formulae

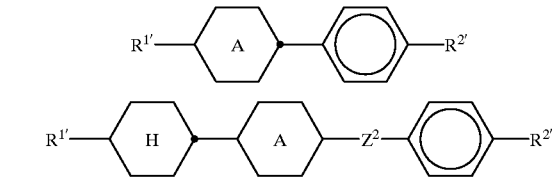

in which
  $R^{1'}$ and $R^{2'}$ are each, independently of one another, alkyl, alkoxy, alkenyl or alkenyloxy having 1–12 carbon atoms,

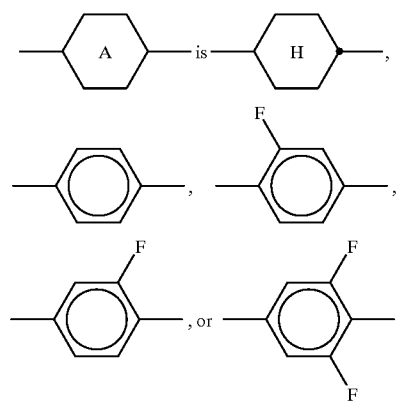

and $Z^2$ is —CH$_2$CH$_2$—, —COO—, —C≡C— or a single bond.

5. A display according to claim 1, wherein the liquid-crystal mixture comprises one or more compounds of formula B 1IIIa B1IIIa

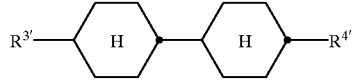

in which
  $R^{3'}$ is CH$_3$—(CH$_2$)$_o$—O—, CH$_3$(CH$_2$)$_p$—, trans—H—(CH$_2$)$_q$—CH=CH—(CH$_2$CH$_2$)$_b$—CH$_2$O— or trans—H—(CH$_2$)$_q$—CH=CH—(CH$_2$CH$_2$)$_b$—, CH$_3$—(CH$_2$)$_o$—O—CH$_2$—,
  $R^{4'}$ is CH$_3$—(CH$_2$)$_p$—,
  o is 1, 2, 3 or 4,
  q is 0, 1, 2, or 3,
  b is 0 or 1, and
  p is 1, 2, 3 or 4.

6. A display according to claim 1, wherein component C comprises one or more compounds selected from the group consisting of those of the formulae V to IX

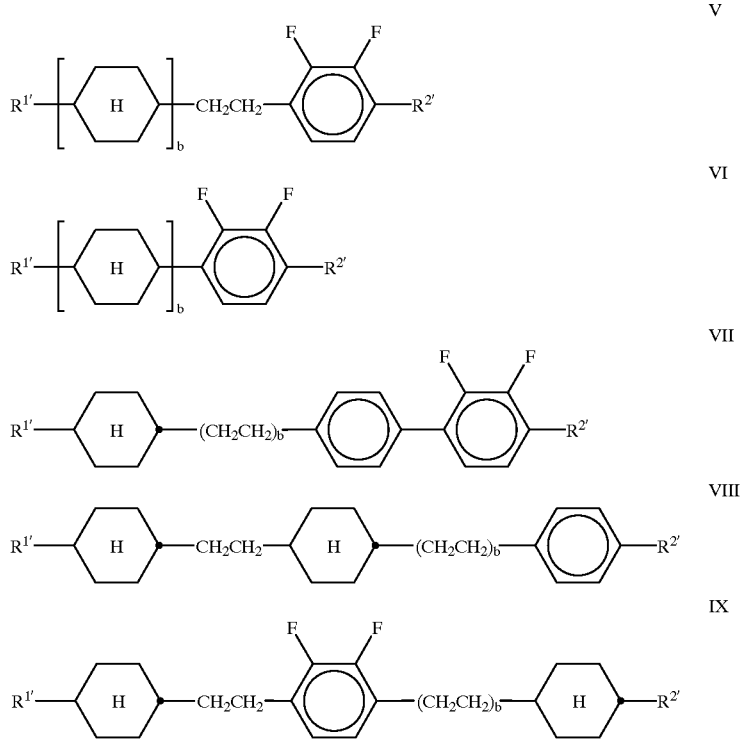

in which $R^{1'}$ and $R^{2'}$ are independently an alkyl group having 1 to 12 carbon atoms, one or two non-adjacent $CH_2$ groups optionally being replaced by —O—, —CH=CH—, —CO—, —OCO— or —COO—, and b is 0 or 1.

7. A display according to claim 1, wherein component B further comprises one or more compounds selected from the group consisting of those of the formulae Xa to XIIa

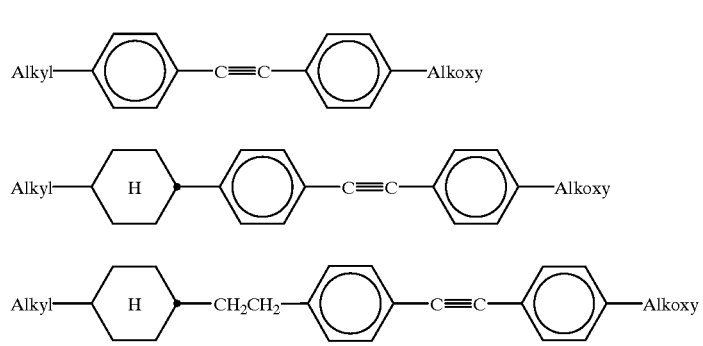

in which the alkyl and alkoxy radicals contain 1 to 7 carbon atoms.

8. A display according to claim 1, wherein component A comprises one or more compounds of the formula T3a

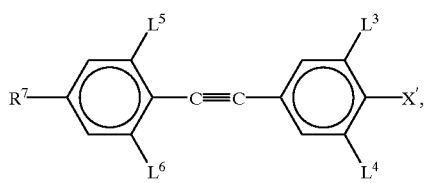

in which $R^7$ is $-C_xH_{2x+1}$, $-OC_xH_{2x+1}$,

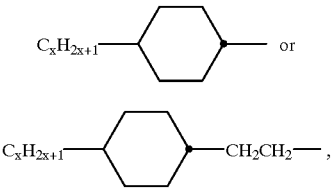 or x is an integer from 1 to 15, $L^{3-6}$ are each, independently of one another, H or F, and X' is F, Cl or $OCF_3$.

9. A display according to claim 1, wherein component B comprises at least one compound of the formula IJ and/or of the formula IK

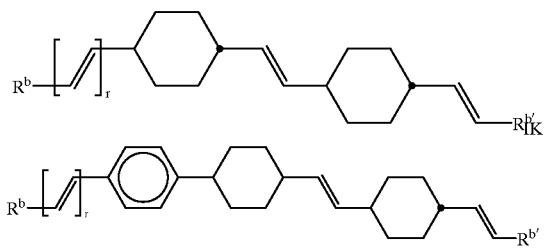

in which $R^b$ and $R^{b'}$ are each, independently of one another, H or alkyl having 1 to 6 carbon atoms, $R^b$ in the case of formula IK where r=0, is alternatively alkoxy having 1 to 6 carbon atoms, and r is 0 or 1.

10. A compound of the formula

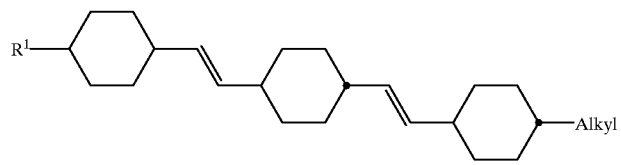

in which $R^1$ is an alkyl, alkoxy or alkenyl radical having 1 to 10 carbon atoms which is unsubstituted or monosubstituted by CN or $CF_3$ or at least monosubstituted by halogen, optionally one or more $CH_2$ groups in this radical being replaced by —O—, and $R^2$ is $(CH_2)_n-CH=CH-R^2$ or $(CH_2)_n-CH=CH_2$, where $R^2$ is a straight chain alkyl of 1 to 6 carbon atoms and n is from 0 to 6.

11. A compound of the formula IB

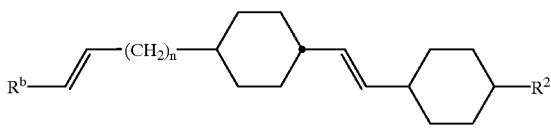

in which $R^1$ is an alkyl, alkoxy or alkenyl radical having 1 to 10 carbon atoms which is unsubstituted or monosubstituted by CN or $CF_3$ or at least monosubstituted by halogen, optionally one or more $CH_2$ groups in this radical being replaced by —O—, and alkyl is an alkyl radical having 1–6 carbon atoms.

12. A compound of the formula IC

IC in which $R^2$ is $(CH_2)_n$—CH=CH—$R^a$ or $(CH_2)_n$—CH=$CH_2$ or $R^a$, where $R^a$ is a straight chain alkyl of 1 to 6 carbon atoms, n is 0–6 and $R^b$ is H or alkyl having 1–6 carbon atoms.

13. A compound of the formula ID

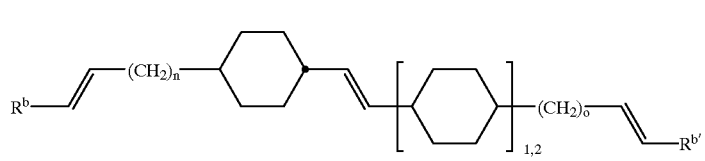

$R^b$ and $R^{b'}$ are each independently of one another H or alkyl having 1–6 carbon atoms, and n and o are each, independently of one another, 0–6.

14. A compound of the formula IE

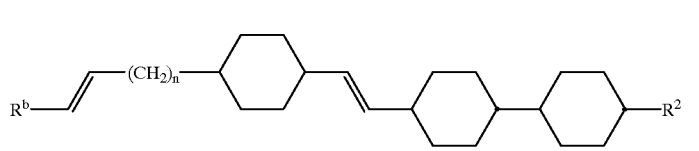

in which $R^2$ is $(CH_2)_n$—CH=CH—$R^a$ or $(CH_2)_n$—CH=$CH_2$ or $R^a$, where $R^a$ is a straight chain alkyl of 1 to 6 carbon atoms, n is 0–6 and $R^b$ is H or alkyl having 1–6 carbon atoms.

15. A compound of the formula IF

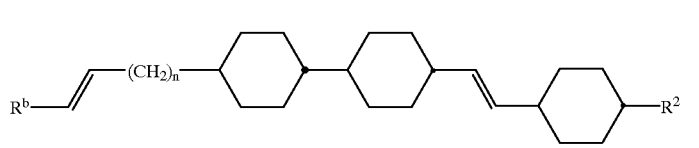

in which $R^2$ is $(CH_2)_n$—CH=CH$R^a$ or $(CH_2)_n$—CH=$CH_2$ or $R^a$, where $R^a$ is a straight chain alkyl or 1 to 6 carbon atoms, n is 0–6, and $R^b$ is H or alkyl having 1–6 carbon atoms.

16. A compound of the formula IG

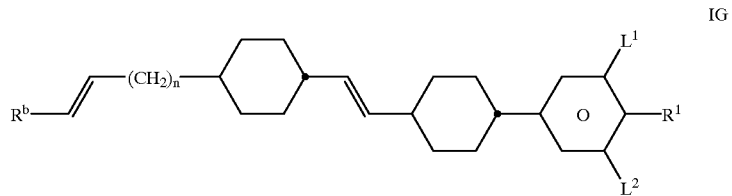

in which $R^1$ is an alkyl, alkoxy or alkenyl radical having 1 to 10 carbon atoms which is unsubstituted or monosubstituted by CN or $CF_2$ or at least monosubstituted by halogen, optionally one or more $CH_2$ groups in this radical being replaced by —O—, n is 0–6, $R^b$ is H or alkyl having 1–6 carbon atoms, and $L^1$ and $L^2$ are H or F.

17. A compound of the formula

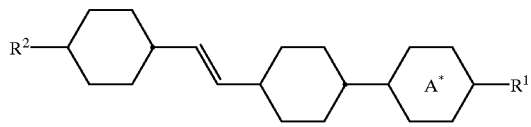

in which
$R^1$ is an alkyl, alkoxy or alkenyl radical having 1 to 10 carbon atoms which is unsubstituted or monosubstituted by CN or $CF_3$ or at least monosubstituted by halogen, optionally one or more $CH_2$ groups in this radical being replaced by —O—,
$R^2$ is $(CH_2)_n$—CH=CH—$R^2$ or $(CH_2)_n$—CH=$CH_2$ or $R^2$, where $R^2$ is a straight chain alkyl of 1 to 6 carbon atoms, n is from 0 to 6,
and

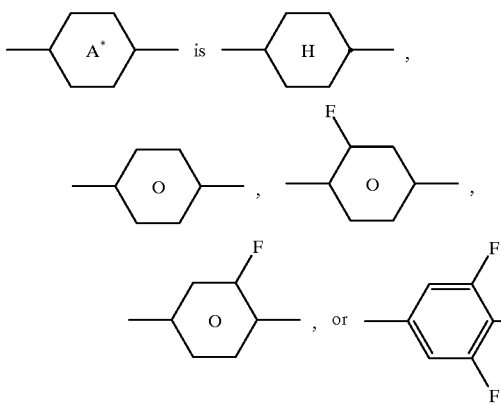

18. Compounds of the formula

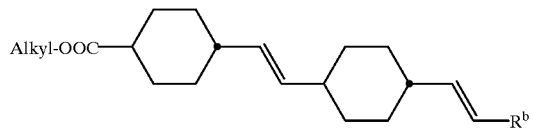

in which
alkyl is $C_{1-6}$-alkyl and
$R^b$ is H or alkyl having 1–6 carbon atoms.

19. A nematic liquid-crystal mixture consisting of
a) 20–90% by weight of a liquid-crystalline component A consisting of one or more compounds having a dielectric anistropy of greater than +1.5;
b) 10–65% by weight of a liquid-crystalline component B consisting of one or more compounds having a dielectric anistropy of between −1.5 and +1.5;
c) 0–20% by weight of a liquid-crystalline component D consisting of one or more compound having a dielectric anisotropy of below −1.5, and
d) an optically active component C in an amount such that the ratio between the layer thickness (separation of the plane-parallel outer plates) and the natural pitch of the chiral nematic liquid-crystal mixture is from about 0.2 to 1.3, wherein component B comprises at least one compound of the formula I

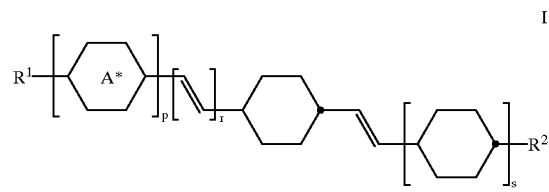

in which

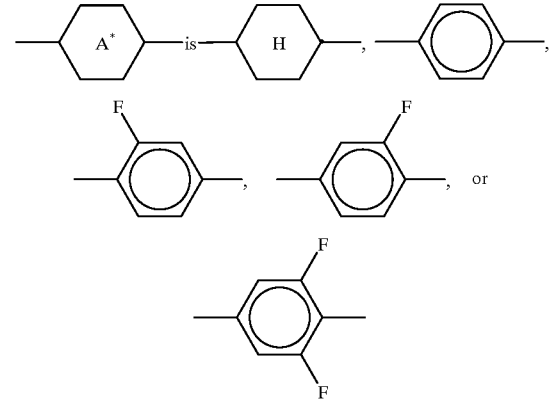

$R^1$ is an alkyl, alkoxy or alkenyl radical having 1 to 10 carbon atoms which is unsubstituted or monosubstituted by CN or $CF_3$ or at least monosubstituted by halogen, optionally one or more $CH_2$ groups in this radical being replaced by —O—,
$R^2$ is $(CH_2)_n$—CH=CH—$R^a$ or $(CH_2)_n$—CH=$CH_2$, and, in the case where r=1, is alternatively $R^a$,
$R^a$ is a straight-chain alkyl having 1–6 carbon atoms,
n is 0–6,
p is 0 or 1,
r is 0 or 1 and
s is 1 or 2.

* * * * *